United States Patent
Garini et al.

(10) Patent No.: US 12,287,240 B2
(45) Date of Patent: Apr. 29, 2025

(54) DEVICE AND METHOD FOR SPECTRAL IMAGING

(71) Applicants: Bar-Ilan University, Ramat-Gan (IL); Tel HaShomer Medical Research Infrastructure and Services Ltd., Ramat-Gan (IL)

(72) Inventors: Yuval Garini, Koranit (IL); Irena Bronshtein-Berger, Jerusalem (IL); Iris Barshack, Tel Aviv-Jaffa (IL)

(73) Assignees: Bar-Ilan University, Ramat-Gan (IL); Tel HaShomes Medical Research Infrastructure and Services Ltd., Ramat-Gan (IL)

( * ) Notice: Subject to any disclaimer, the term of this patent is extended or adjusted under 35 U.S.C. 154(b) by 354 days.

(21) Appl. No.: 17/582,741

(22) Filed: Jan. 24, 2022

(65) Prior Publication Data

US 2022/0146311 A1    May 12, 2022

Related U.S. Application Data

(63) Continuation of application No. PCT/IL2020/050827, filed on Jul. 24, 2020.
(Continued)

(51) Int. Cl.
*G01J 3/28* (2006.01)
*G01J 3/46* (2006.01)
*G01J 3/06* (2006.01)

(52) U.S. Cl.
CPC ............ *G01J 3/2823* (2013.01); *G01J 3/462* (2013.01); *G01J 2003/066* (2013.01); *G01J 2003/2826* (2013.01)

(58) Field of Classification Search
CPC .... G01J 3/2823; G01J 3/462; G01J 2003/066; G01J 2003/2826; G01J 3/0208;
(Continued)

(56) References Cited

U.S. PATENT DOCUMENTS

| 6,160,618 A | 12/2000 | Garner |
| 6,690,817 B1 * | 2/2004 | Cabib ................. G01N 33/582 382/165 |

(Continued)

FOREIGN PATENT DOCUMENTS

WO    WO 2021/014455    1/2021

OTHER PUBLICATIONS

International Preliminary Report on Patentability Dated Feb. 3, 2022 From the International Bureau of WIPO Re. Application No. PCT/IL2020/050827. (8 Pages).
(Continued)

*Primary Examiner* — Jonathan M Hansen

(57) ABSTRACT

A spectral imaging device includes an imager, a scanning stage to establish relative motion between the imager and a sample in a scanning direction and an optical system controlling a light characteristic of a light beam constituting an image of the sample to the imager. The optical system includes a light varying element to receive the light beam and provide an output light beam with spatially varying light characteristic over a cross-section thereof. A set of redirecting optical elements direct light rays from the sample to form the light beam, and to focus the output light beam onto the imager. A controller controls the scanning stage and the imager to capture a plurality of image frames with an overlap including a defined shift that is greater than 1 pixel along the scanning direction between consecutive image frames. A computing device consolidates image data to provide an image of the sample.

**10 Claims, 26 Drawing Sheets
(13 of 26 Drawing Sheet(s) Filed in Color)**

Related U.S. Application Data

(60) Provisional application No. 62/877,858, filed on Jul. 24, 2019.

(58) Field of Classification Search
CPC .... G01J 3/0289; G01J 2003/1234; G01J 3/12; A61B 1/00172
See application file for complete search history.

(56) References Cited

U.S. PATENT DOCUMENTS

| | | | |
|---|---|---|---|
| 6,887,711 | B1* | 5/2005 | Diem ................ G01N 15/1456 436/171 |
| 2002/0135769 | A1 | 9/2002 | Lewis et al. |
| 2007/0024946 | A1 | 2/2007 | Panasyuk et al. |
| 2018/0184015 | A1 | 6/2018 | Richarte et al. |
| 2018/0188173 | A1* | 7/2018 | Scarcelli ............ G01N 15/1429 |
| 2018/0373017 | A1 | 12/2018 | Dixon |
| 2019/0195690 | A1* | 6/2019 | Ben-Shahar .............. G06T 7/90 |

OTHER PUBLICATIONS

Communication Pursuant to Rule 124(4) EPC Dated Jul. 24, 2023 From the European Patent Office Re. Application No. 209843117.1. (12 pages).

Kumar et al. "Novel System for Measuring Giant Spectral Images and its Application for Cancer Detection", Proceedings vol. 10068, Imaging, Manipulation, and Analysis of Biomolecules, Cells, and Tissues XV; 100680N (2017), SPIE BiOS, San Francisco, California, United States, Feb. 16, 2017. Abstract.

International Search Report and the Written Opinion Dated Dec. 28, 2020 From the International Searching Authority Re. Application No. PCT/IL2020/050827. (15 Pages).

Invitation to Pay Additional Fees and Communication Relating to the Results of the Partial International Search Dated Nov. 16, 2020 From the International Searching Authority Re. Application No. PCT/IL2020/050827. (4 Pages).

Akbari et al. "Detection of Cancer Metastasis Using a Novel Macroscopic Hyperspectral Method", Proceedings of SPIE—The International Society for Optical Engineering, 8317: 831711-1-831711-7, Published Online Mar. 23, 2012.

Barducci et al. "Theoretical Aspects of Fourier Transform Spectrometry and Common Path Triangular Interferometers", Optics Express, 18(11): 11622-11649, Published Online May 18, 2010.

Boucheron et al. "Utility of Multispectral Imaging for Nuclear Classification of Routine Clinical Histopathology Imagery", BMC Cell Biology, 8(Suppl.1): S8-1-S8-11, Published Online Jul. 10, 2007.

Farris et al. "Whole Slide Imaging for Analytical Anatomic Pathology and Telepathology", Archives of Pathology & Laboratory Medicine, 141(4): 542-550, Published Online Feb. 12, 2017.

Ferrec et al. "Optimal Geometry for Sagnac and Michelson Interferometers Used as Spectral Imagers", Optical Engineering, 45(11): 11560-1-11560-6, Nov. 2006.

Garini et al. "Spectral Imaging: Methods, Design, and Applications", Biomedical Optical Imaging Technologies, Biological and Medical Physics, Biomedical Engineering Book Series, Chap.4: 11-161, Published Online Aug. 28, 2012.

Ghaznavi et al. "Digital Imaging in Pathology Whole-Slide Imaging and Beyond", The Annual Review of Pathology, 8: 331-359, Published Online Nov. 15, 2012.

Irshad et al. "Multispectral Band Selection and Spatial Characterization: Application to Mitosis Detection in Breast Cancer Histopathology", Computerized Medical Imaging and Graphics, 38(5): 390-402, Published Online Apr. 24, 2014.

Khouj et al. "Hyperspectral Imaging and K-Means Classification for Histologic Evaluation of Ductal Carcinoma In Situ", Frontiers in Oncology, 8(Art. 17): 1-8, Published Online Feb. 7, 2018.

Levenson et al. "Multispectral Imaging in Biology and Medicine: Slices of Life", Cytometry Part A, 69A(8): 748-758, Published Online Sep. 12, 2006.

Levenson et al. "Spectral Imaging in Preclinical Research and Clinical Pathology", Analytical Cellular Pathology, 35(5-6): 339-361, Published Online Apr. 4, 2012.

Lindner et al. "Rapid Microscopy Measurement of Very Large Spectral Images", Optics Express, 24(9): 9511-9527, Published Online Apr. 22, 2016.

Liu et al. "A Comparative Performance Analysis of Multispectral and RGB Imaging on HER2 Status Evaluation for the Prediction of Breast Cancer Prognosis", Translational Oncology, (6): 521-530, Published Online Nov. 8, 2016.

Lu et al. "Medical Hyperspectral Imaging: A Review", Journal of Biomedical Optics, 19(1): 010901-1-010901-23, Published Online Jan. 20, 2014.

Madabushi "Digital Pathology Image Analysis: Opportunities and Challenges", Imaging in Medicine, 1(1): 7-10, Oct. 2009.

Minami "Fourier Transform Spectroscopy Using Image Sensors", Mikrochimica Acta, 93(1-6): 309-324, Jan. 1987.

Mukhopadhyay et al. "Whole Slide Imaging Versus Microscopy for Primary Diagnosis in Surgical Pathology. A Multicenterblinded Randomized Noninferiority Study of 1992 Cases (Pivotal Study)", The American Journal of Surgical Pathology, 42(1): 39-52, Jan. 2018.

Pust "Innovative Filter Solutions for Hyperspectral Imaging. Linear Variable Bandpass Filters Specifically Designed for Hyoperspectral Imaging", Optik & Photonik, 11(3): 24-27, Jun. 2016.

Sellar et al. "Effects of Aberrations on Spatially Modulated Fourier Transform Spectrometers", Optical Engineering, 33(9): 3087-3092, Sep. 1994.

Zhao et al. "Multichannel FT-Raman Spectroscopy: Noise Analysis and Performance Assessment", Applied Spectroscopy, 51(11): 1687-1697, Nov. 1997.

Supplementary European Search Report and the European Search Opinion Dated Nov. 20, 2023 From the European Patent Office Re. Application No. 20843117.1. (15 Pages).

Zimmerman et al. "Automatic Classification of Cancer Cells in Multispectral Microscopic Images of Lymph Node Samples", 2016 38th Annual International Conferenve of IEEE Engineering in Medicine and Biology Society, p. 3973-3976, Aug. 16, 2016.

* cited by examiner

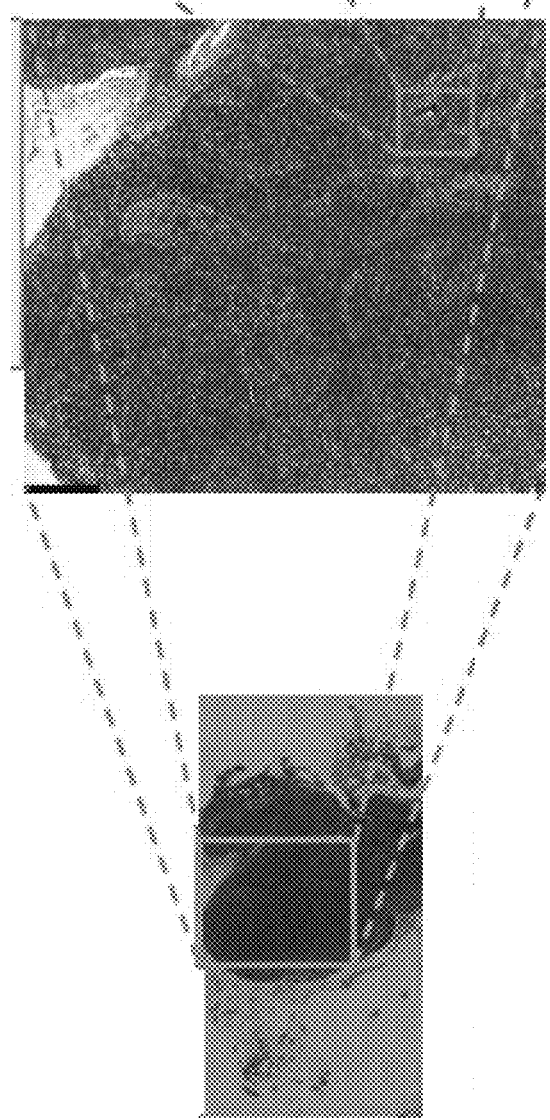
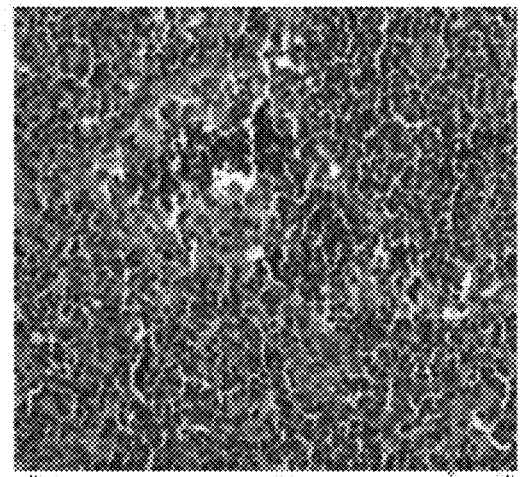
FIG. 19A  FIG. 19B  FIG. 19C

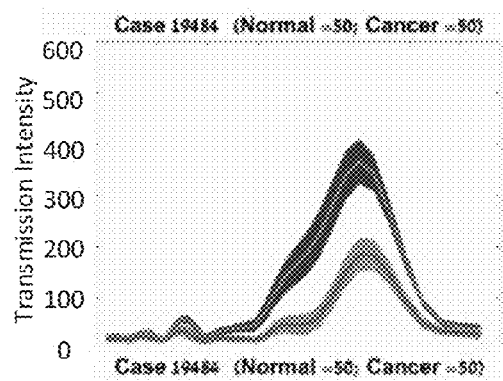
FIG. 23A
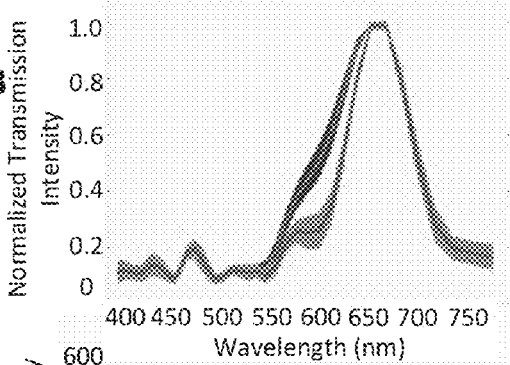
FIG. 23B
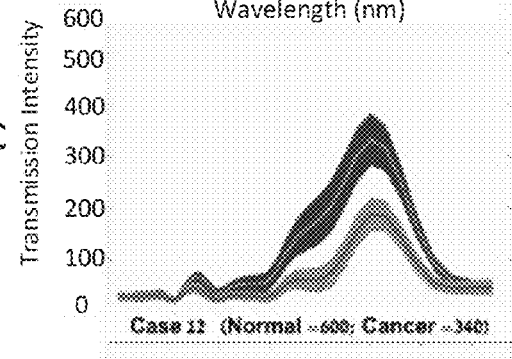
FIG. 23C
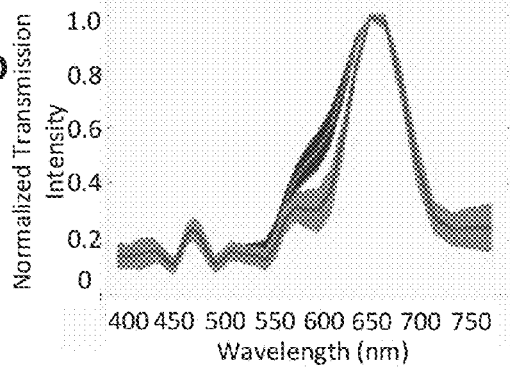
FIG. 23D
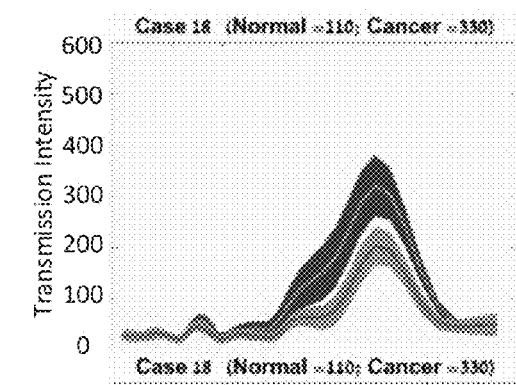
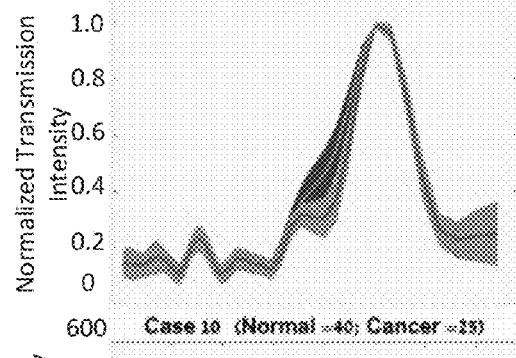
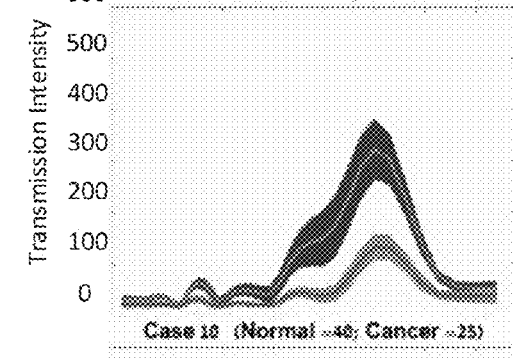
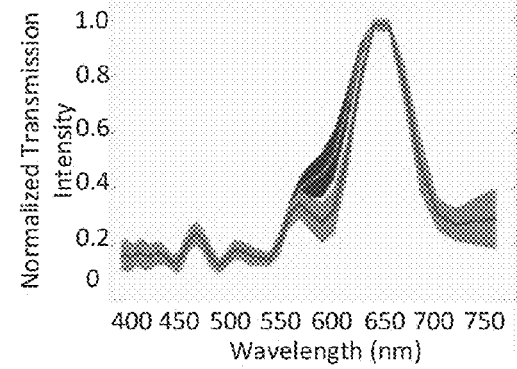

DEVICE AND METHOD FOR SPECTRAL IMAGING

RELATED APPLICATION/S

This application is a Continuation of PCT Patent Application No. PCT/IL2020/050827 having International filing date of Jul. 24, 2020, which claims the benefit of priority under 35 USC § 119(e) of U.S. Provisional Patent Application No. 62/877,858 filed on Jul. 24, 2019.

The contents of the above applications are all incorporated by reference as if fully set forth herein in their entirety.

FIELD AND BACKGROUND OF THE INVENTION

The present invention, in some embodiments thereof, relates to imaging and, more particularly, but not exclusively, to measurement of physical information from an object that is more than the eye can see, such as light polarization and spectrum of a whole image, which can be used, for example, in digital pathology, such as, but not limited to, whole slide imaging.

Digital pathology allows tissue samples to be easily viewed, managed, shared and analyzed on a computer monitor. Presently, digital pathology is a tool that helps pathologist improve throughput as well as quality of analyses being performed.

Whole slide imaging (WSI) refers to the technology behind digital pathology. WSI includes both the technology for scanning glass slides to generate a digital image as well as software for handling the often large amount of image data captured during the scanning. The software processes, stores and displays the scanned data. A pathologist may then perform the analysis based on the images displayed by the software.

In known WSI, the slides are typically scanned with a red-green-blue (RGB) image sensor. RGB imaging provides a fast, available and cost efficient method for imaging the relatively large field of view that is typically associated with WSI.

Nevertheless, RGB imaging only measures a degenerated part of the information that is available on the object and misses most of the information, such as the spectrum of each point of the image, its polarization properties and its real dynamic range (the exact intensity). Spectral imaging refers to the measurement of images while providing for each point of the sample (or each pixel in the obtained digital image) a spectrum in a certain spectral range, e.g., a visible range (400-700 nm) and a certain spectral resolution, e.g., 1-20 nm. A spectral image thus contains much more information compared to an RGB image and may be used for various analyses of the measured samples.

Known spectral imaging systems include, for example, stop-go systems and push-broom systems. In stop-go systems, the area of a sample is divided into small sub-regions and each of a plurality of sub-regions of the sample is imaged a plurality of times with an array of different color filters. The imaging is performed in a consecutive manner after each switch of the color filter and each step movement to capture a different sub-region. After all the sub-regions are imaged with all the filters, the images is tiled together to obtain a spectral image of the sample.

Push broom scanning systems offer a more continuous process in which an entire spectrum of a single line from the sample is captured in each image. The scanner then advances one line at a time to scan the entire sample.

SUMMARY OF THE INVENTION

The inventors found that although digital pathology today may provide some improvement in throughput as well as quality of analyses performed by a pathologist, this improvement is limited. The inventors realized that for a significant increase in throughput, as well as quality of analysis, a fully automated analysis and/or machine-aided diagnostics is required. The inventors realized that one of the obstacles toward reaching automated analysis of various pathological parameters and even machine-aided diagnostics is the loss of information when using RGB imaging, which covers only a portion of the spectral information included in the slide.

The inventors found that conventional methods for multispectral imaging are not typically suitable for the field of digital pathology due to the large size of samples being imaged that requires a large field of view, as well as the need for quick and cost effective imaging methods that can be applied for bulk analysis. The inventors found that stop and go systems typically have rather long measuring duration due to the repetitive stop and go process and the constant switch between filters or other hardware-related dispersion element. The inventors found that push broom scanning systems also have rather long measuring duration especially for the relatively large field of view that is typically associated with WSI. Furthermore, the inventors found that the amount of data accumulated per sample in both stop and go and push broom systems is tremendous.

According to some example embodiments, there is provided a device and method for acquiring a spectral image. The device and method according to some embodiments of the present invention are suitable for WSI. In some example embodiments, the device includes a fiberscope that may be used to capture spectral images in vivo. For example, the device may be used during a medical procedure, e.g. surgery to image tissue and identify cancer regions in the tissue. The image may be inspected during the medical procedure. Optionally, the medical personal can determine what part of the tissue to remove or treat based on the spectral information detected during the medical procedure.

It is appreciated that although embodiments of the present invention may be configured to be suitable for WSI, use of the devices and methods for spectral imaging of samples other than slides are also contemplated in some embodiments of the present invention.

According to some example embodiments, the device and method provide on-the-fly scanning with a spectrum at each pixel using a leapfrog scanning method. According to some example embodiments, a plurality of images is captured over the scanning duration, wherein each of the images covers a two dimensional region of the sample with variations in light characteristics across the respective image. The variations may include, for example, variations in spectral bands, polarization, and/or intensity and are effected by a dedicated optical system. The plurality of images is optionally and preferably captured to include overlap between consecutive frames with a shift, or leap, between the images that is larger than 1 pixel, e.g., 3-200 pixels or more preferably 10-200 pixels. Based on this leapfrog scanning method, a same point in the sample being imaged is captured more than once over the course of scanning, each time with different light characteristics. At the end of the scanning procedure, the data accumulated may be consolidated to provide the light characteristics (e.g., a spectrum, an intensity, a polarization, a phase) at each pixel of the image of the sample. Optionally, whole histological and/or cytological slides are scanned through a microscope with a scanning stage. In this manner large images with good spectral and spatial resolutions may be obtained. Polarization of light contains information on the structure of the object and can also be used for analysis of the measured objects.

According to some example embodiments, there is provided a method to automate the identification of cell nuclei in a spectral image. The spectral image can be acquired using any spectral imaging technique, but is optionally and preferably acquired based on the device and method described herein. Optionally, the identification is based at least in part on spectral characteristics of the image. In some embodiments of the present invention the identification is based on both spectral characteristics and morphological characteristics, and in some embodiments of the present invention the identification is based on spectral characteristics but not on morphological characteristics. Optionally, the tissue sample is a lymph node sample of breast cancer biopsy.

According to some example embodiments, there is provided a method to perform automated analysis and/or machine-aided diagnostics with digital pathology. In some example embodiments, the automated analysis includes automated analysis of spectral images of nuclei in the sample and classification of the cells and/or the tissue based on the analysis. Optionally, the classification is into one of two populations of cells. For example, the classification includes identifying cells as either belonging to a cancerous population of cells or non-cancerous population of cells. In some embodiments of the present invention, the non-cancerous population is normal population. Optionally, the tissue sample is a lymph node sample of breast cancer biopsy.

Optionally the objects of the image such as cells, nuclei and different cell type are identified according to multiple parameters analyzed from the measured images, including the spectral information, polarization information, shape and morphological information.

According to some example embodiments, the device and method may be used for protein expression profiling. In some example embodiments, a plurality of proteins may be labeled, for example, using one or more chromophores (for transmission microscopy), or using one or more florescent dyes (for florescent microscopy), and the spectral data captured during imaging may be used to identify the labeled proteins and evaluate intensity of their expression in each cell. Optionally, the protein expression profiling may be applied for personalized medicine applications. In some embodiments of the present invention the labeling is combinatorial labeling [see, e.g., Ried et al., "Simultaneous Visualization of Seven Different DNA Probes by In Situ Hybridization Using Combinatorial Fluorescence and Digital Imaging Microscopy", Proc. Natl. Acad. Sci., 1388-1392 (1992)].

Optionally, the analysis of measurement of multiple probe labeling includes identification of cell type, measuring the level of intensity of each of the labeled proteins in each cell or its different compartments, and providing an expression profile of the proteins for each cell type. Similar analysis may be performed on original cancerous tissue and the same tissue after treating it with a biochemical content, thereby analyzing the changes of the statistics of the cell types and the expression types of these cell types.

According to an aspect of some example embodiments, there is provided a spectral imaging device including: an imager configured to capture image frames; a scanning stage configured to establish relative motion between the imager and a sample in a scanning direction; and an optical system configured to control a light characteristic of a light beam constituting an image of the sample to the imager, the optical system including: a light varying element configured to receive the light beam and provide an output light beam having a spatially varying light characteristic over a cross-section thereof; and a set of redirecting optical elements configured to direct light rays from the sample to form the light beam, and to focus the output light beam onto the imager; and a controller configured to control the scanning stage and the imager to capture a plurality of image frames with movement of the scanning stage in a scanning direction, wherein the plurality of image frames is captured with an overlap including a defined shift that is greater than 1 pixel along the scanning direction between consecutive image frames in the plurality of image frames.

Optionally, a computing device configured to consolidate image data from the plurality of image frames to provide an image of the sample.

Optionally, the light characteristic includes a wavelength and the image of the sample is a spectral image.

Optionally, the light characteristic includes a polarization.

Optionally, the light characteristic includes intensity.

Optionally, the light characteristic includes phase.

Optionally, the light characteristic includes spatial intensity modulation in parallel to or perpendicular to the scanning axis.

Optionally, the controller is configured to scan the sample during continuous relative motion between the imager and the sample.

Optionally, the defined shift is based on coordinating a scanning speed with a frame rate of the imager and wherein the controller is configured to perform the coordination.

Optionally, the light varying element includes a linearly variable color filter.

Optionally, the light varying element is selected from a group including: an interferometer, a circular variable filter, a filter of color bands, a liquid crystal variable filter, an acousto-optic variable filter, a prism, a grating, and a holographic device.

Optionally, the light varying element includes an array of different light varying elements aligned in the scanning direction.

Optionally, the array of different light varying elements is configured to vary at least two light characteristics selected from a group including: a wavelength, a polarization, an intensity, a spatial modulation, and a phase.

Optionally, the optical system is configured to direct the light beam penetrating through a working range of the light varying element on to the imager, wherein the working range is at least two times larger than a point spread function of the light beam at least in one dimension.

Optionally, the optical system is configured to spread the light beam originating from a point in the sample toward the light varying element in a cross scan direction, wherein the cross scan direction is perpendicular to the scan direction.

Optionally, the optical system is configured to focus the light beam originating from a point in the sample toward the light varying element in a direction parallel to the scan direction.

Optionally, the optical system is configured to defocus the light beam originating from a point in the sample on the light varying element in the scan direction over a defined area on the light varying element.

Optionally, the set of redirecting optical elements is a set of lenses.

Optionally, the set of lenses includes a pair of spherical lens and wherein the light varying element is positioned therebetween.

Optionally, focal lengths of the pair of spherical lenses are matched.

Optionally, the set of lenses includes a pair of cylindrical lenses on either side of spectrally varying element and on either side of the pair of spherical lenses.

Optionally, the set of redirecting optical elements are diffractive optical elements.

Optionally, the set of redirecting optical elements includes a beam expander.

Optionally, the device includes an autofocus device configured to change position of the sample with respect to the detector maintain focus over a measurement duration.

Optionally, the device includes an illumination source and wherein the controller is configured to control operation of the illumination source.

Optionally, the illumination source is configured to provide pulsed illumination.

Optionally, the computing device is configured to construct a spectral image based on the image data captured.

Optionally, the controller is configured to provide less than one pixel shift over a duration that an image frame is being captured based on controlling speed of the scanning stage.

Optionally, the imager is configured with a frame rate of 50-5000 frames/sec.

Optionally, the scanning stage is configured to advance at a rate of 0.001-100 mm/sec.

According to an aspect of some example embodiments, there is provided a spectral imaging device including: an imager configured to capture image frames; a scanning stage configured to establish relative motion between the imager and a sample in a scanning direction; and an optical system configured to control a light characteristic of a light beam constituting an image of the sample to the imager, the optical system including: a light varying element configured to receive the light beam and provide an output light beam having a temporal varying light characteristic; and a set of redirecting optical elements configured to redirect light rays directed from the sample to form the light beam, and to focus the output light beam onto the imager; and a controller configured to control the scanning stage, the light varying element and the imager to capture a plurality of image frames with movement of the scanning stage in a scanning direction and with changes in the light characteristics that span a defined spectrum, wherein the plurality of image frames is captured with an overlap including a defined shift that is greater than 1 pixel along the scanning direction between consecutive image frames in the plurality of image frames.

Optionally, a computing device configured to consolidate image data from the plurality of image frames to provide an image of the sample.

Optionally, the controller is configured to synchronize changes in the light characteristics actuated by the light varying element with capturing of the plurality of image frames.

Optionally, a rate at which a light varying element alters the light characteristic is similar to the frame rate of the imager.

Optionally, the light varying element is a time varying color filter.

Optionally, the light varying element is a liquid crystal tunable filter (LCTF) or an acousto-optic tunable filter (AOTF).

Optionally, the computing device is configured to construct a spectral image based on the image data captured.

According to an aspect of some example embodiments, there is provided a method of capturing a spectral image of a sample, the method including: establishing relative motion between an imager and a sample in a scanning direction; temporally varying a light characteristic of a light beam constituting an image of the sample; and capturing by the imager a plurality of image frames during the motion with an overlap including a defined shift that is greater than 1 pixel along the scanning direction between consecutive image frames in the plurality of image frames.

Optionally, the method includes consolidating image data from the plurality of image frames to provide an image of the sample.

Optionally, the method includes dynamically focusing the sample with respect to the detector.

Optionally, the method includes synchronizing changes in the light characteristics actuated by the light varying element with capturing of the plurality of image frames.

Optionally, the light varying element is a liquid crystal tunable filter (LCTF) and wherein the varying of the light characteristic is based on tuning a voltage of the LCTF.

Optionally, the light varying element is an acousto-optic tunable filter (AOTF) and wherein the varying of the light characteristic is based on tuning a frequency of the AOTF.

According to an aspect of some example embodiments, there is provided a method of capturing a spectral image of a sample, the method including: establishing relative motion between an imager and a sample in a scanning direction; spatially varying a light characteristic of a light beam constituting an image of the sample; and capturing by the imager a plurality of image frames during the motion with an overlap including a defined shift that is greater than 1 pixel along the scanning direction between consecutive image frames in the plurality of image frames.

Optionally, the method includes consolidating image data from the plurality of image frames to provide an image of the sample.

Optionally, the light characteristic is selected from a group including at least one of: wavelength, polarization, intensity, spatial modulation and phase.

Optionally, the method includes focusing the light beam originating from a point in the sample toward the light varying element in the scan direction; and spreading the light beam originating from a point in the sample toward the light varying element in a cross scan direction.

Optionally, the method includes defocusing the light beam originating from a point in the sample on the light varying element in the scan direction over a defined area on the light varying element; and spreading the light beam originating from a point in the sample toward the light varying element in a cross scan direction.

According to an aspect of some example embodiments, there is provided a method of analyzing a spectral image of a sample having cells stained by a stain, the method including: identifying in the spectral image a plurality of nuclei, and extracting, for each nucleus, a spectrum characterizing an optical transmission and absorbance of the nucleus within a wavelength range corresponding to the stain, thereby providing a plurality of spectra, one spectrum for each nucleus of at least a portion of the nuclei; comparing shapes of the spectra thereamongst; identifying each nucleus of the portion of the nuclei, as belonging to one of at least a first population of nuclei and a second population of nuclei based on the comparing; and marking the nucleus according to the identification.

Optionally, the method includes identifying each nucleus of the portion of the nuclei, as belonging to one of the first population, the second population and a third population of nuclei, wherein the third population is a set of multiple types of nuclei.

According to an aspect of some example embodiments, there is provided a method of analyzing a spectral image of a sample having cells stained by a stain, the method including: identifying in the spectral image a plurality of nuclei, and extracting, for each nucleus, a spectrum characterizing an optical absorbance of the nucleus within a wavelength range corresponding to the stain, thereby providing a plurality of spectra, one spectrum for each nucleus of at least a portion of the nuclei; for each nucleus of the portion of the nuclei, comparing a shape of a respective spectrum to a shape of at least one of a first reference spectrum representing a first population and a second reference spectrum representing a second population; identifying each nucleus of the portion of the nuclei, as belonging to one of at least the first population of nuclei and the second population of nuclei based on the comparing; and marking the nucleus according to the identification.

Optionally, the method includes identifying each nucleus of the portion of the nuclei, as belonging to one of the first population, the second population and a third population of nuclei, wherein the third population is a set of multiple types of nuclei.

Optionally, the third population represents cells excluded from the first population and from the second population.

Optionally, the first population is cancerous cells and the second population is normal cells.

Optionally, the cancerous cells are selected from a group including atypical, carcinoma, sarcoma, lymphoma and leukemia cells.

Optionally, the first reference spectrum is annotated as corresponding to cancerous nuclei.

Optionally, the second reference spectrum is annotated as corresponding to non-cancerous nuclei.

Optionally, the sample is stained with one or multiple stains, and optionally the stains includes hematoxylin.

Optionally, the spectrum is normalized.

Optionally, the method further includes calculating mean square error relative to a reference spectrum, wherein the comparison is based on the mean square error.

Optionally, the method further includes calculating a ratio between mean square error relative to a first reference spectrum and mean square error relative to a second reference spectrum, wherein the comparison is based on the ratio.

Optionally, the first reference spectrum is annotated as corresponding to cancerous nuclei, and the second reference spectrum is annotated as corresponding to non-cancerous nuclei.

Optionally, each mean square error is calculated using non-normalized quantities.

Optionally, each mean square error is calculated using normalized quantities.

Optionally, the method further includes calculating a first ratio, and a second ratio; wherein each ratio is defined between a mean square error relative to a first reference spectrum and a mean square error relative to a second reference spectrum, the first reference spectrum being annotated as corresponding to cancerous nuclei, and the second reference spectrum being annotated as corresponding to non-cancerous nuclei; wherein each mean square error in the first ratio is calculated using non-normalized quantities, and each mean square error in the second ratio is calculated using normalized quantities; and wherein the comparison is based on the ratios.

Optionally, the method further includes representing the spectra as a vector in multi-dimensional space; and computing vectorial properties of the spectra in each dimension of the multi-dimensional space, wherein a parameter associated with spectral intensity is the vectorial properties of the spectra in each dimension of the multi-dimensional space.

Optionally, the method includes estimating the level of chromatin in cells belonging to the each population.

Optionally, the method further includes capturing the spectral image. Optionally, the capturing includes the method described herein above.

According to an aspect of some example embodiments, there is provided a spectral imaging device comprising: an imager configured to capture image frames; an optical system configured to control a light characteristic of a light beam constituting an image of tissue to the imager, the optical system comprising: a light varying element configured to receive the light beam and provide an output light beam having a spatially varying light characteristic over a cross-section thereof or a temporal varying light characteristic; a set of redirecting optical elements configured to direct light rays from the tissue to form the light beam, and to focus the output light beam onto the imager; and a fiberscope configured to direct the light beam constituting the image of the tissue to the imager, wherein the fiberscope is configured to be manually manipulated for scanning the sample; and a controller configured to: control the imager to capture a plurality of image frames as the fiberscope is manually moved across the tissue; perform image registration between the plurality of images; consolidate image data from the plurality of image frames based on the image registration to provide an image of the tissue; and display the image.

Optionally, the light characteristic comprises a wavelength and the image of the sample is a spectral image.

Optionally, the light varying element is selected from a group including: an interferometer, a circular variable filter, a liquid crystal variable filter, an acousto-optic variable filter, a prism, a grating, and a holographic device, a liquid crystal tunable filter (LCTF) or an acousto-optic tunable filter (AOTF).

According to an aspect of some example embodiments, there is provided a method for protein expression profiling, the method comprising: labeling a plurality of proteins in a sample having cells stained by a stain; imaging the sample in accordance with the method described herein above; constructing a spectral image based on the imaging; identifying cancer cells and healthy cells in the spectral image; detecting intensity of protein expression in the cancer cells and in the healthy cells based on spectral data from the spectral image; and generating an output pertaining to said detection.

Optionally, the method includes labeling two proteins with a same label and distinguishing between the expression of the two proteins based on a spatial location of the expression in the cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified block diagram of a spectral imaging device suitable for WSI in accordance with some example embodiments;

FIGS. 2A and 2B are simplified schematic top and side view respectively of an example optical system for the spectral imaging device in accordance with some example embodiments;

FIG. 3 is a schematic representation of an example light varying element for the optical system in accordance with some example embodiments;

FIGS. 4A, 4B and 4C are schematic representations of three consecutive scanning positions and corresponding captured frames, all in accordance with some example embodiments;

Figure 5A:
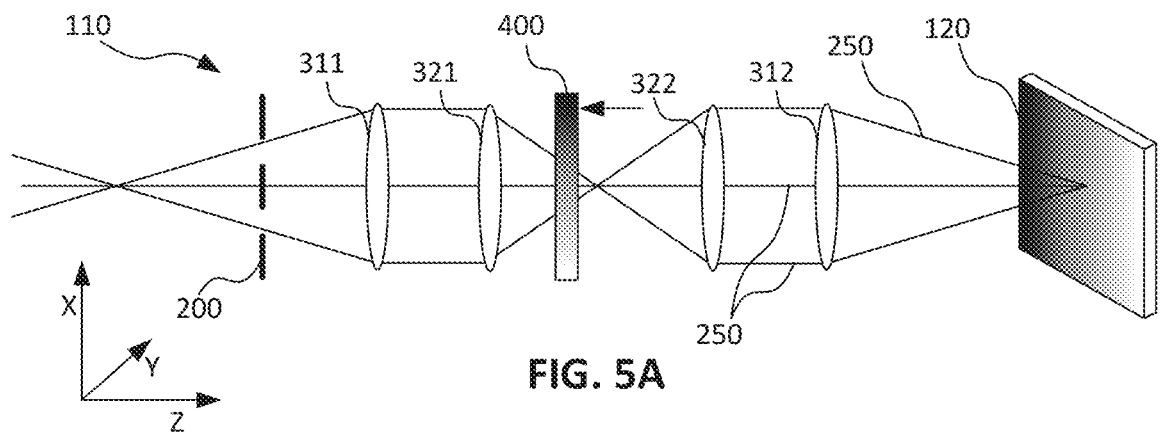
Figure 5B:
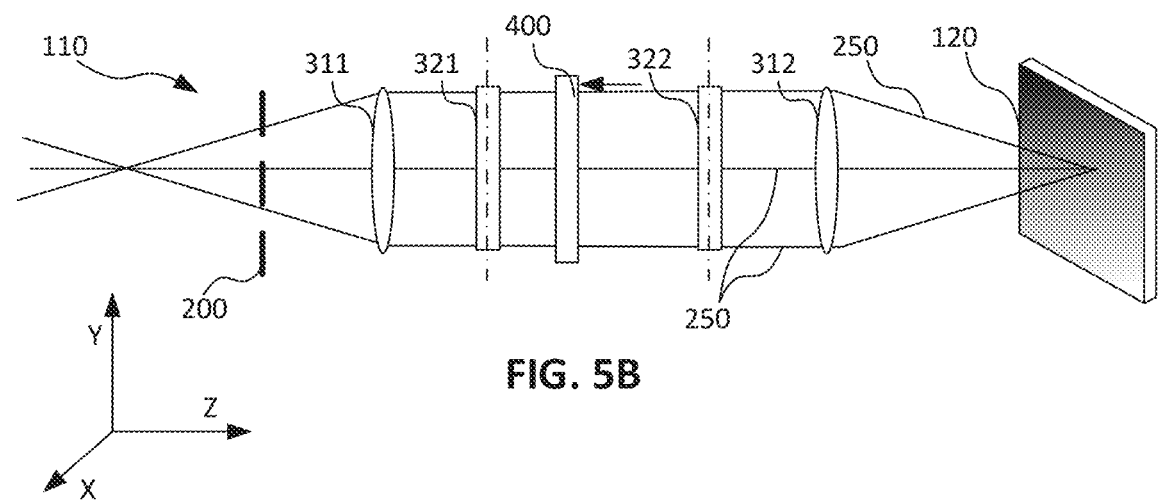
Figure 6:
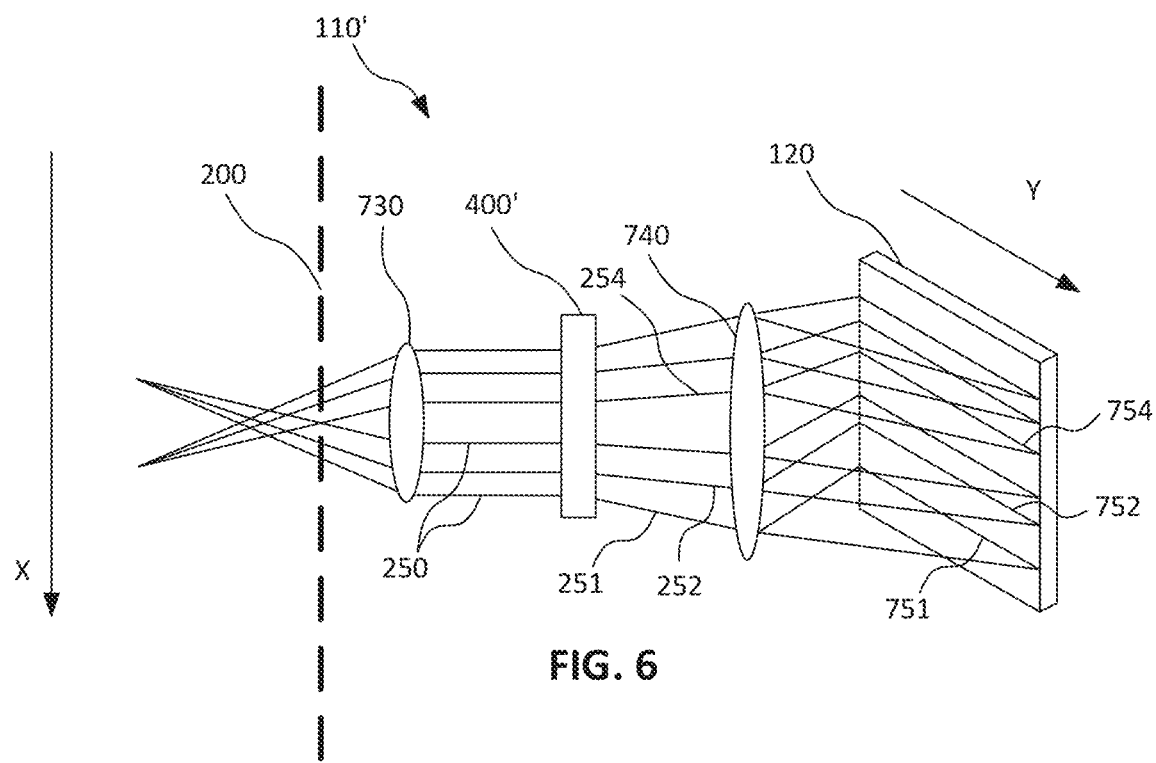
Figure 7:
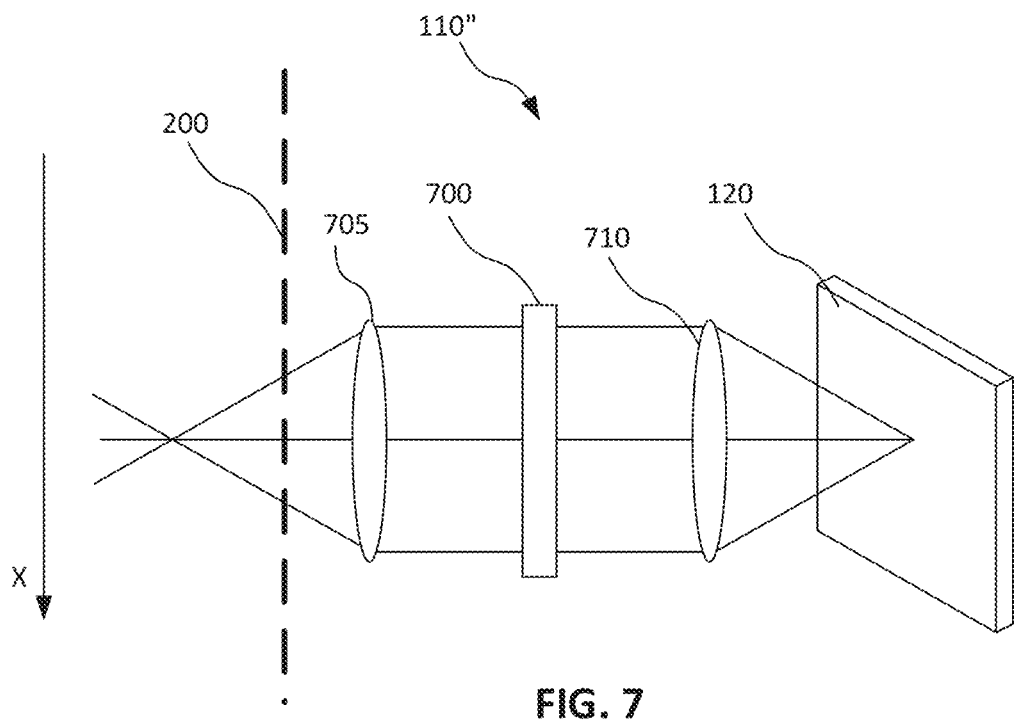
Figure 8:
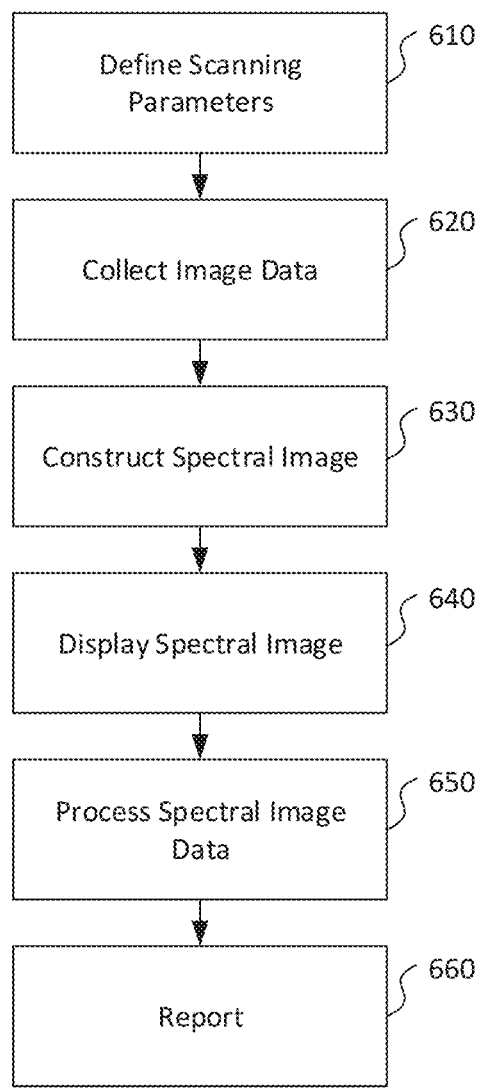
Figure 9:
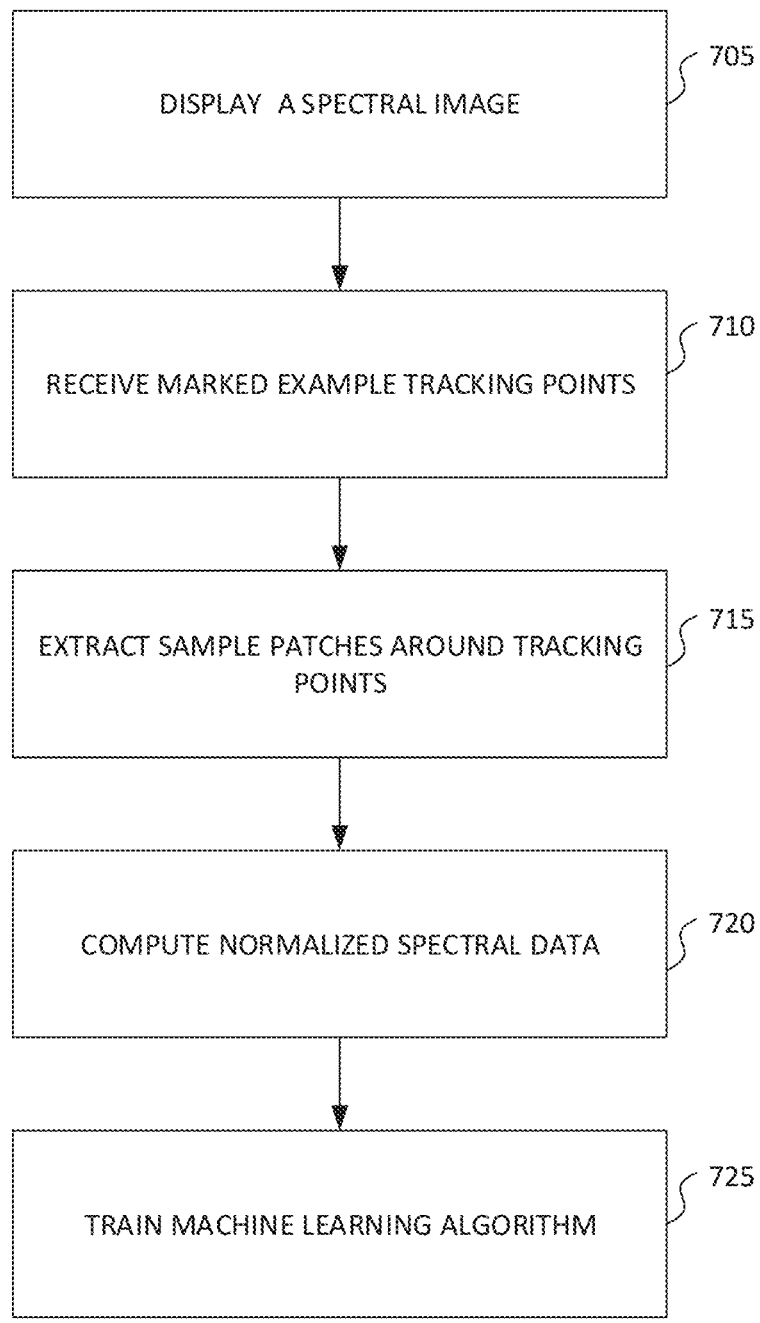
Figure 10:
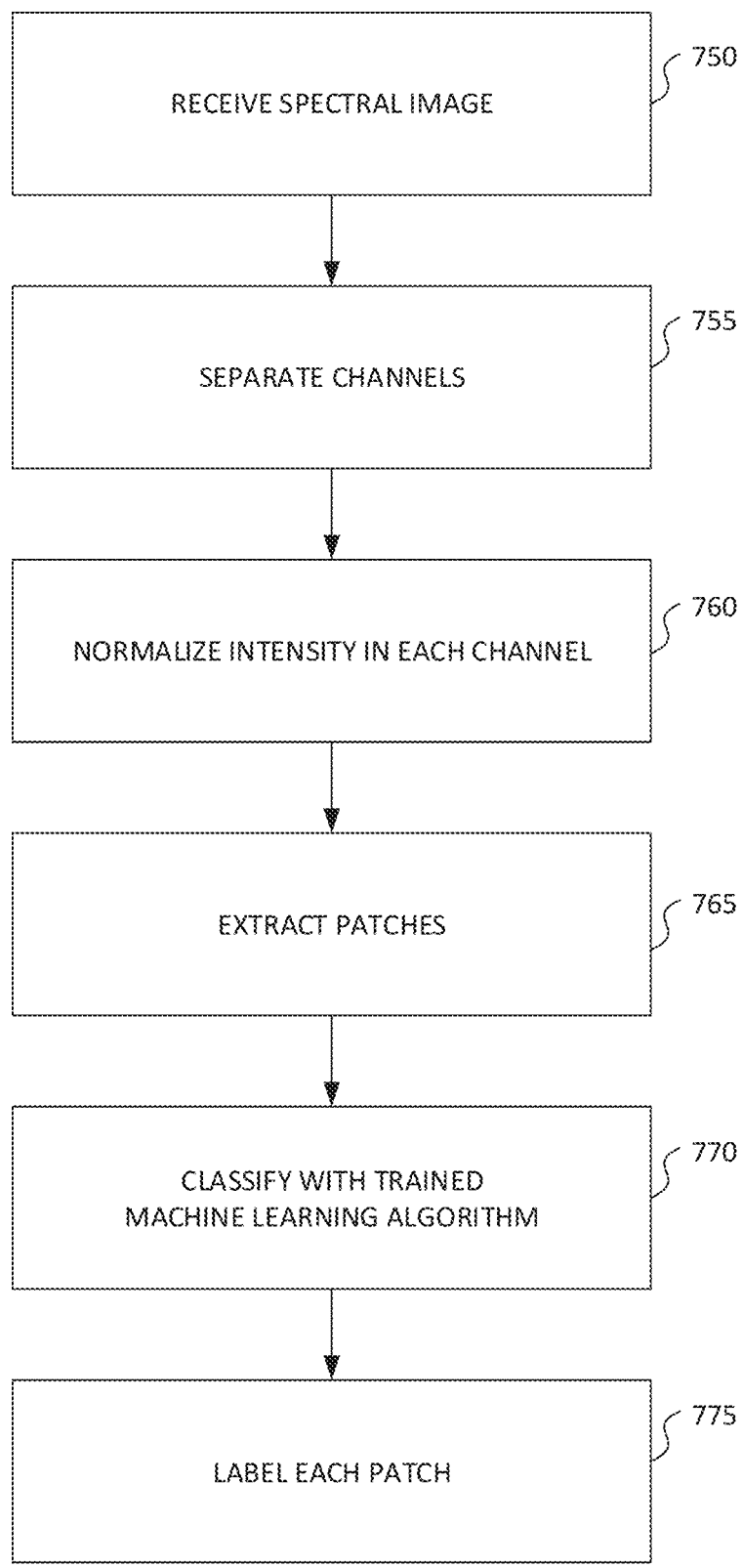
Figure 11A:
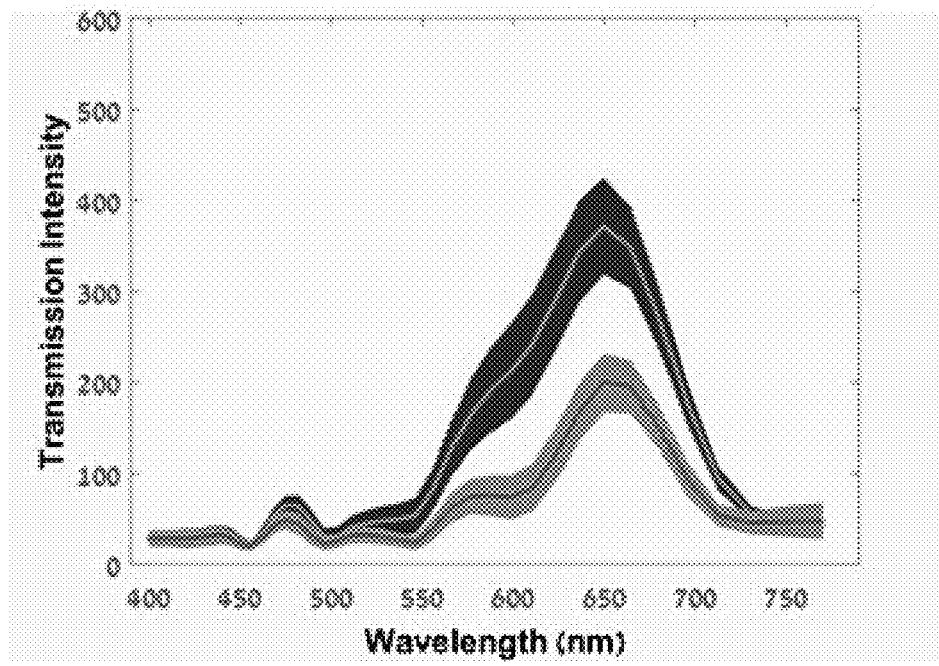
Figure 11B:
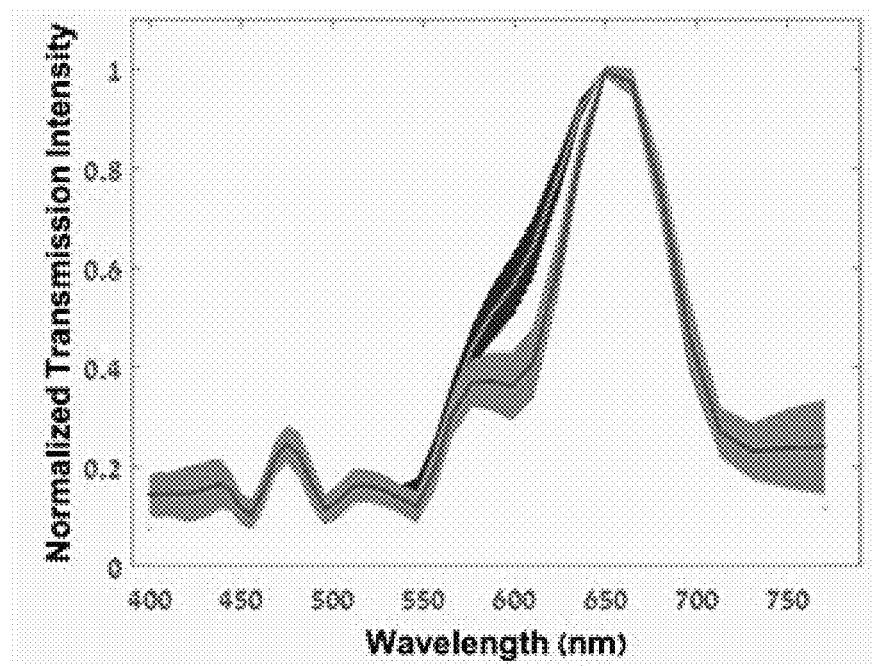
Figure 12A:
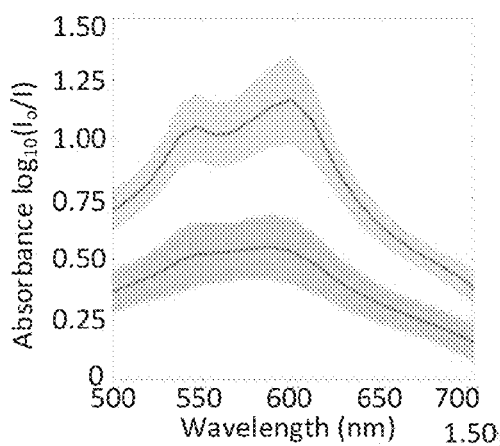
Figure 12B:
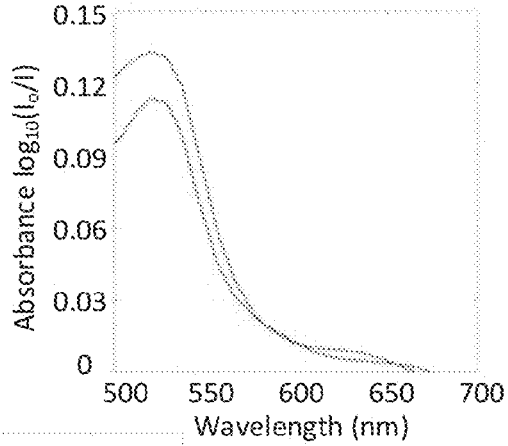
Figure 12C:
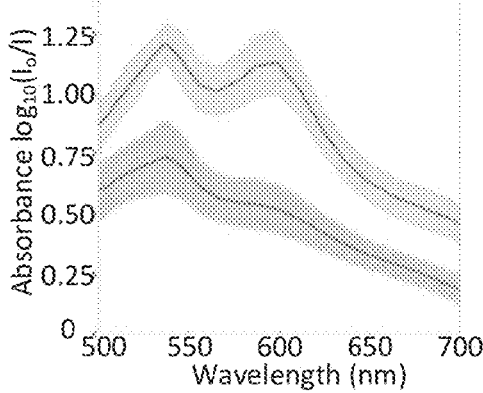
Figure 14:
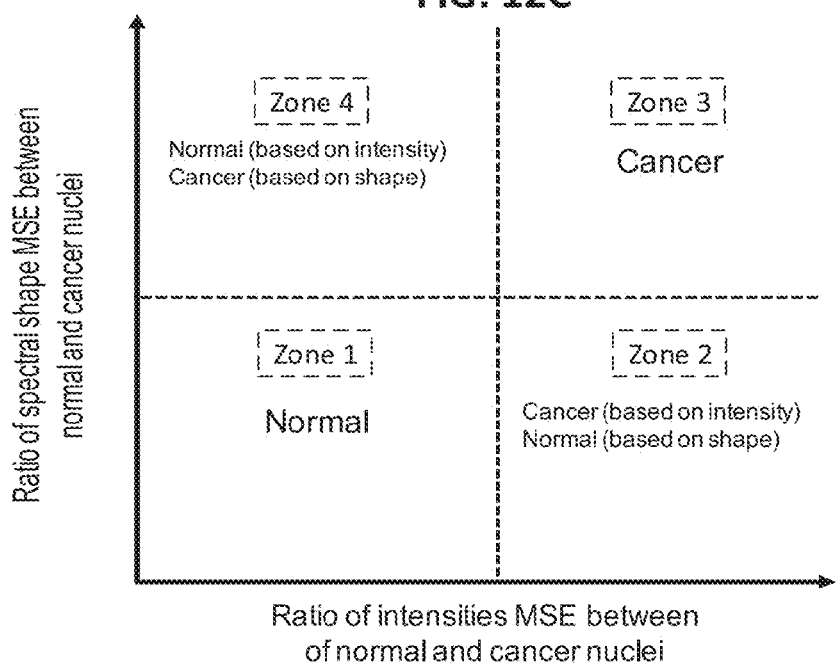
Figure 13:
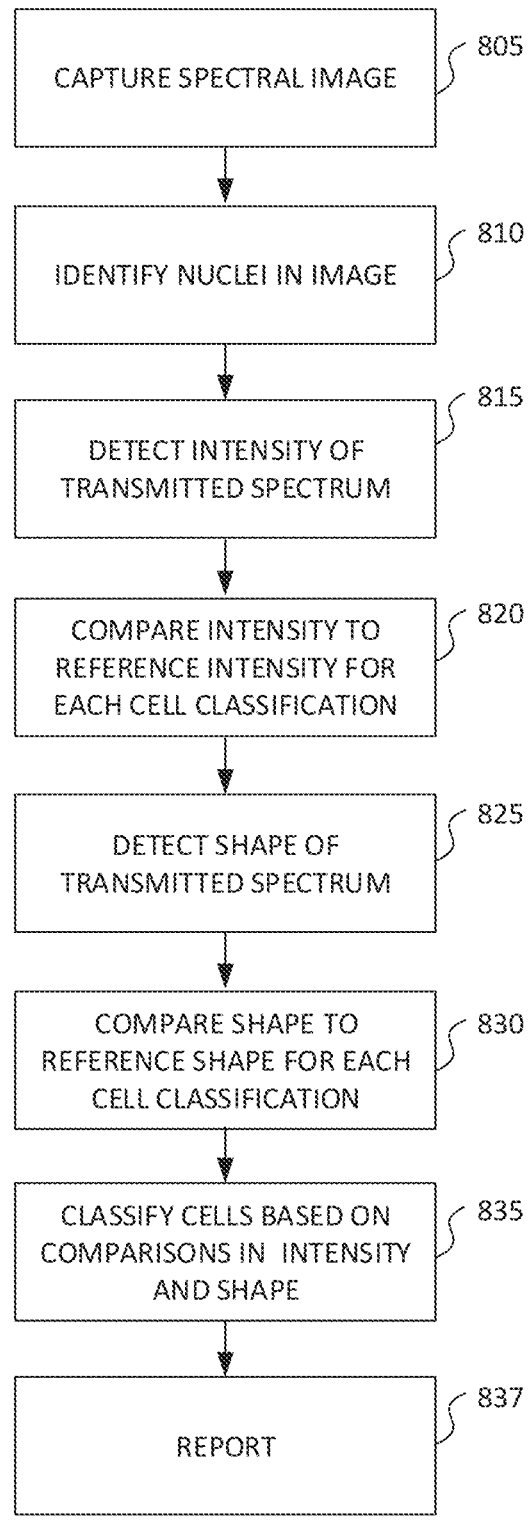
Figure 15:
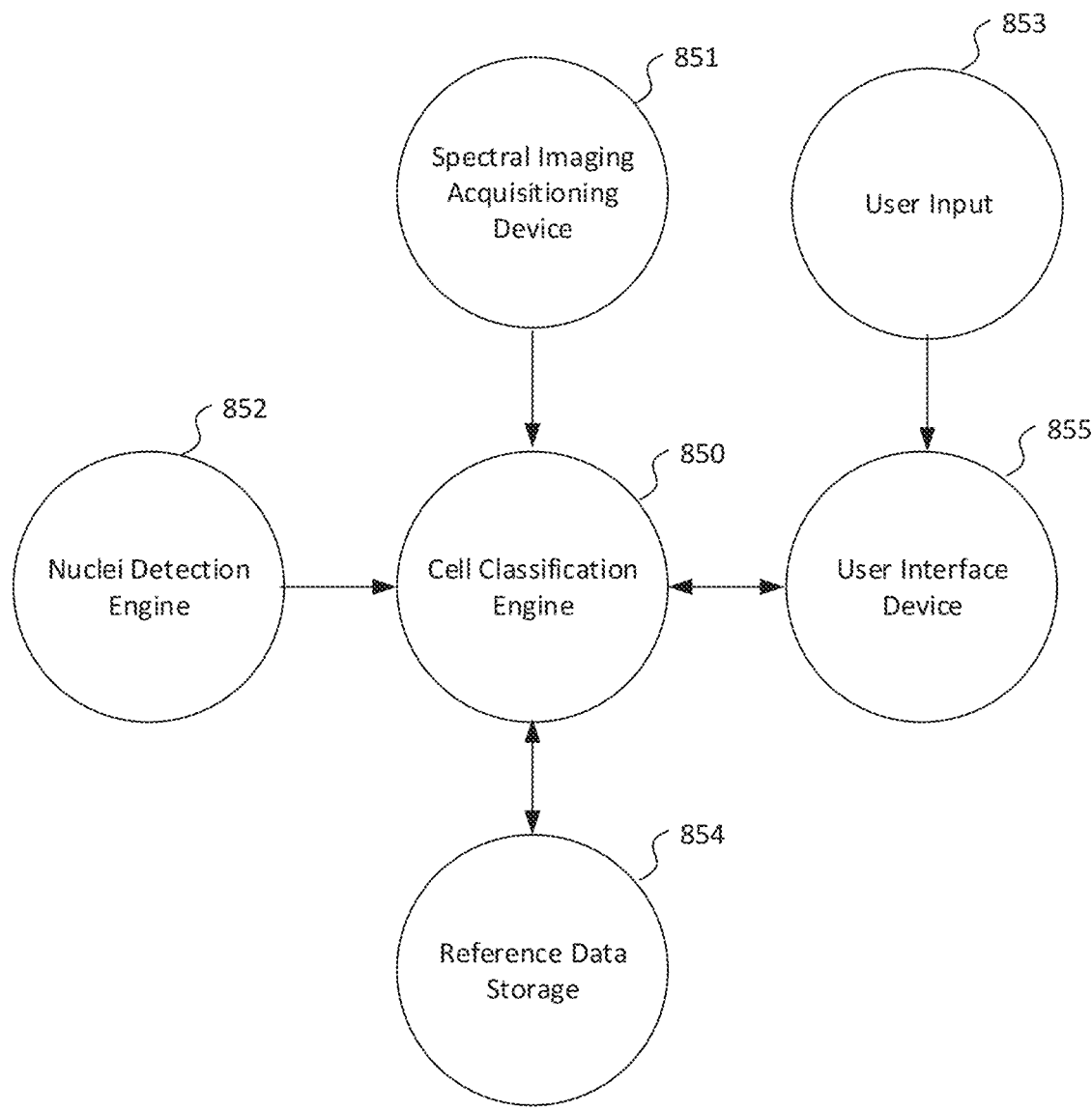
Figure 16A:
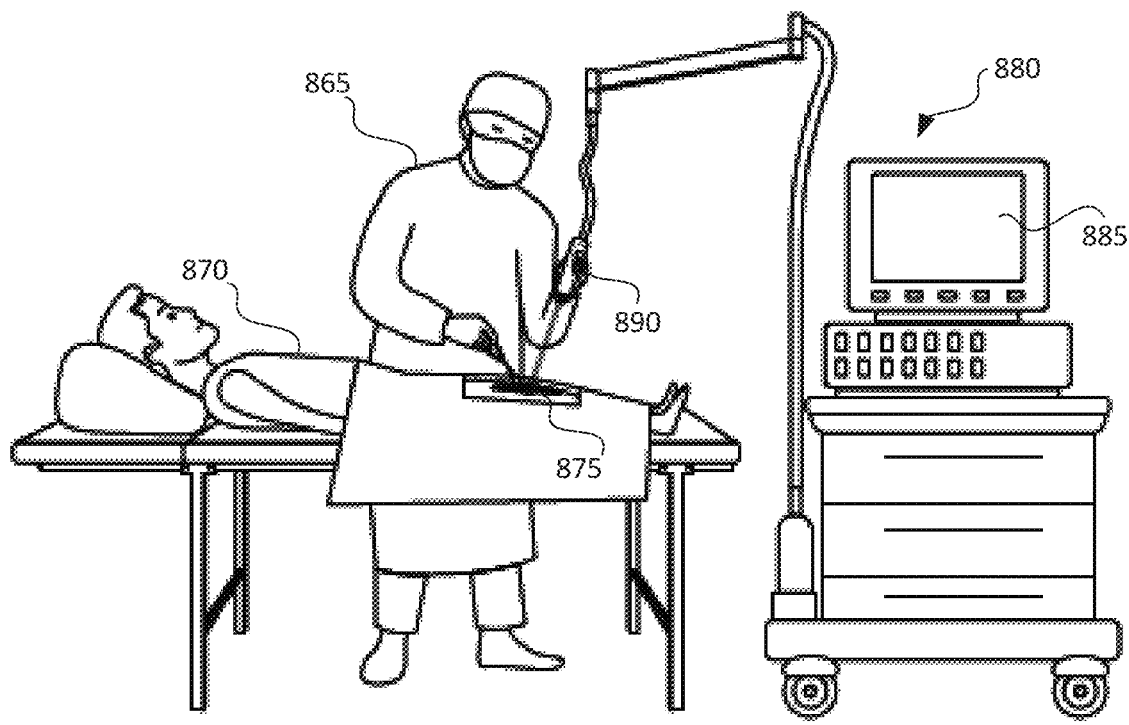
Figure 16B:
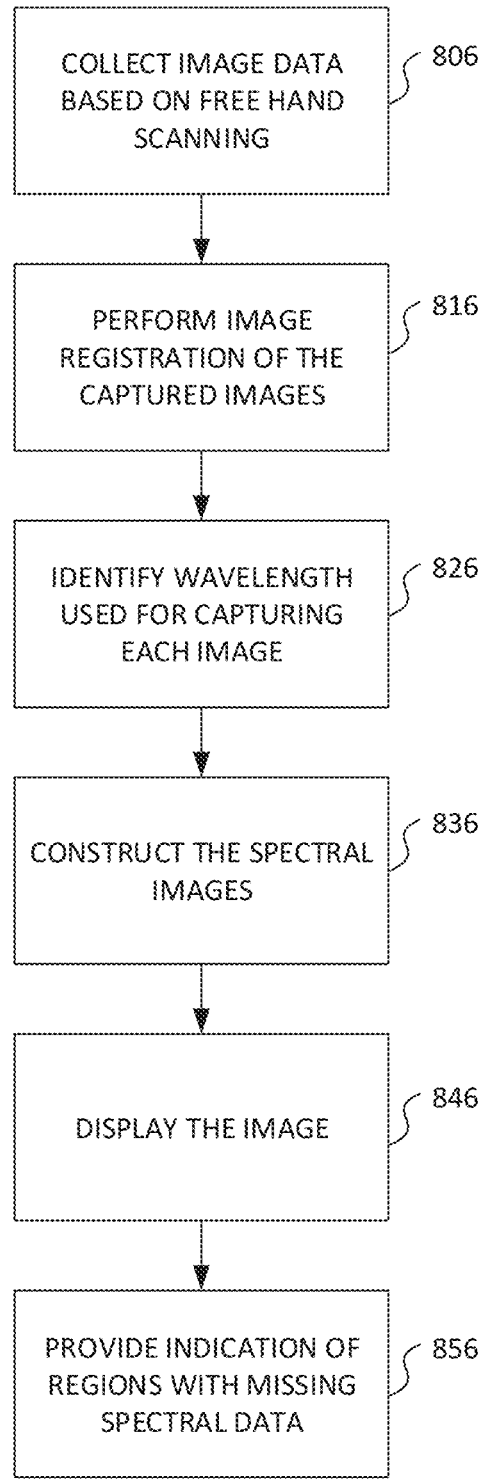
Figure 17:
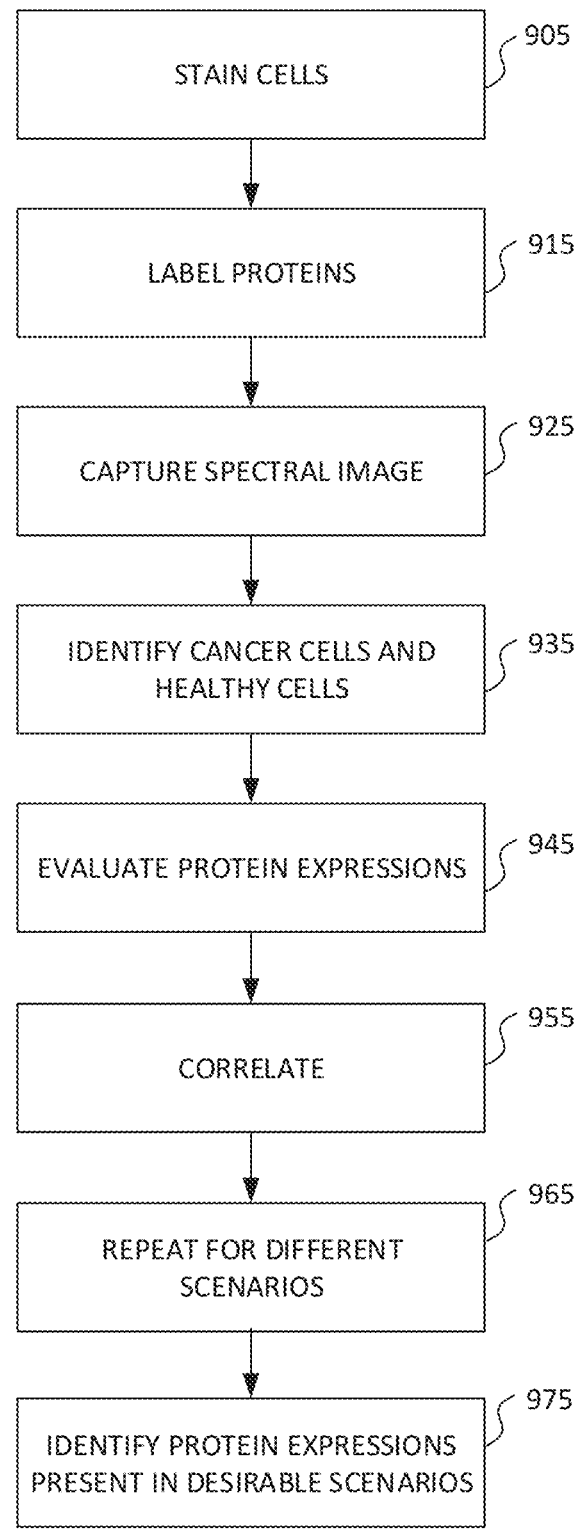
Figure 18:
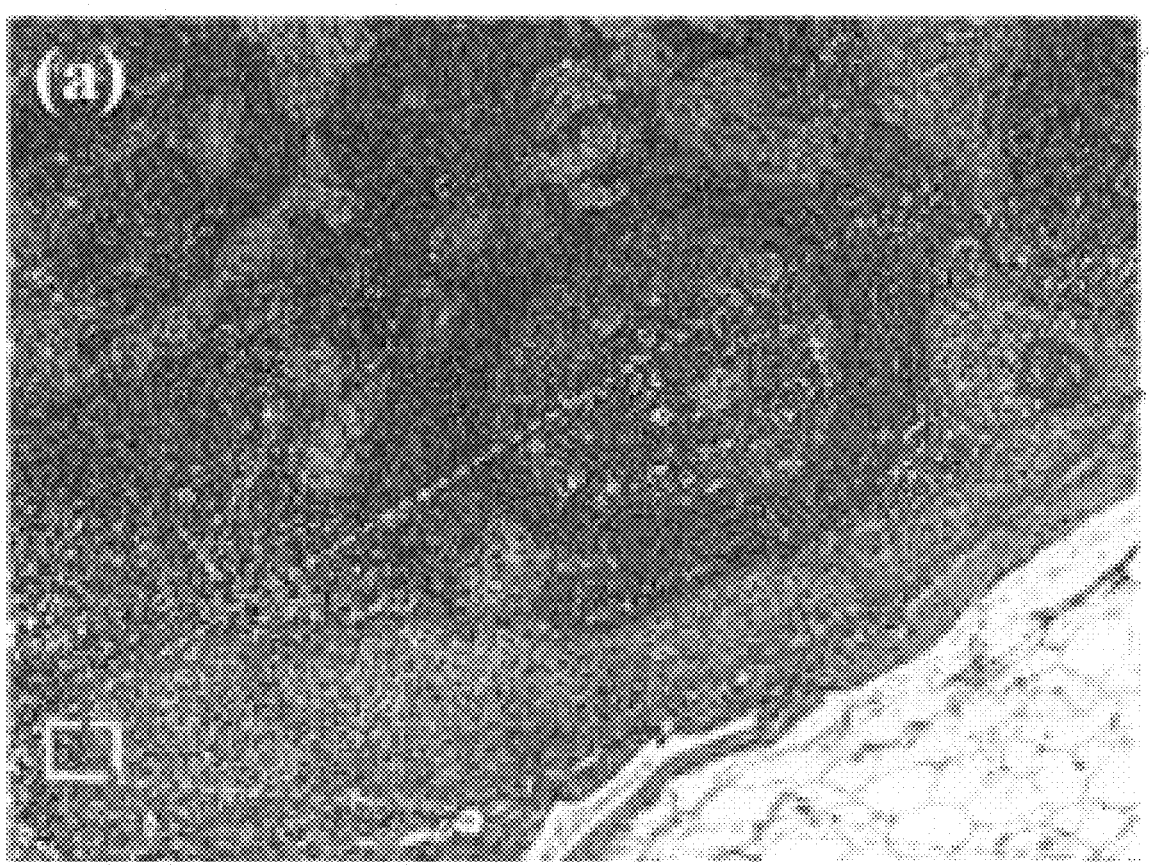

FIGS. 5A and 5B showing a simplified schematic top and side view respectively of an example optical system for measuring spectral images with high spectral resolution that is adapted for measuring spectral images with relatively low spectral resolution in accordance with some example embodiments;

FIG. 6 is simplified schematic representation of another example optical system spectral imaging suitable for WSI in accordance with some example embodiments;

FIG. 7 is simplified schematic representation of time varying optical system for spectral imaging that is suitable for WSI in accordance with some example embodiments;

FIG. 8 is a simplified flow chart of an example method for spectral imaging that is suitable for WSI in accordance with some example embodiments;

FIG. 9 is a simplified flow chart of an example method to train a machine learning process in accordance with some example embodiments;

FIG. 10 is a simplified flow chart of an example method to identify nuclei in a sample with automated detection in accordance with some example embodiments;

FIGS. 11A and 11B are example graph comparing measured transmission spectra and normalized transmission spectra respectively for normal and cancer nuclei in accordance with some example embodiments;

FIGS. 12A, 12B, 12C are absorption spectra of normal and cancer nuclei stained with a specific dye in accordance with some example embodiments;

FIG. 13 is a simplified flow chart of an example method for classifying nuclei based on spectral intensity and spectral shape in accordance with some example embodiments;

FIG. 14 is a schematic representation of an example classification scheme for differentiating between cancer and normal cells, in accordance with some example embodiments;

FIG. 15 is a simplified schematic representation of an example spectral imaging acquisition system including a cell classification engine in accordance with some example embodiments;

FIG. 16A is a schematic drawing of an example spectral imaging acquisition system including a fiberscope in accordance with some example embodiments;

FIG. 16B is a simplified flow chart of an example method for constructing a spectral image with free hand scanning in accordance with some example embodiments;

FIG. 17 is a simplified flow chart of an example method to identify protein expressions analysis for cancer treatment in accordance with some example embodiments;

FIG. 18 is a small part of a spectral image that contains 5000×6000 pixels captured based on the device and method as described herein and in accordance with some example embodiments.

Figures 20A, 20B:
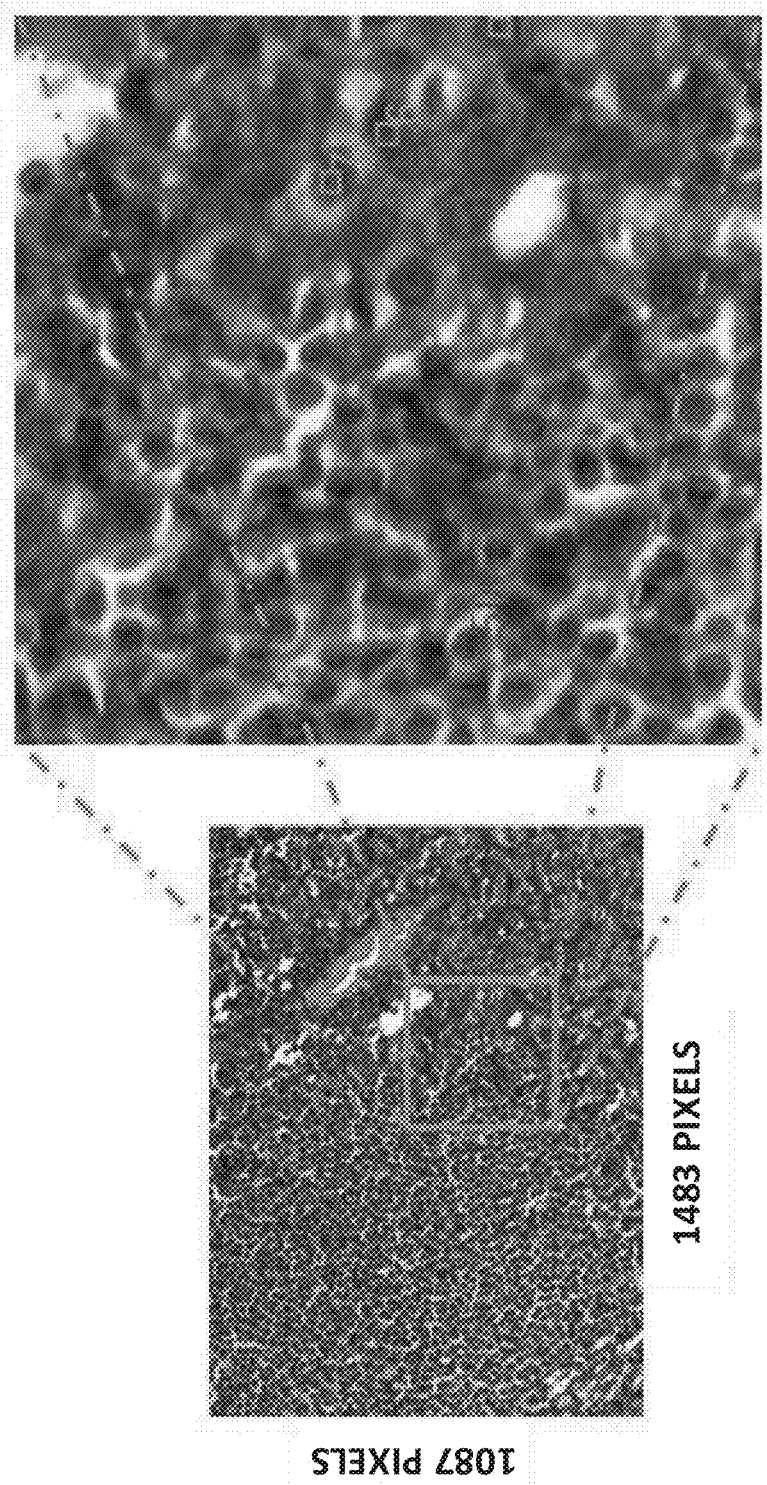
Figure 22A:
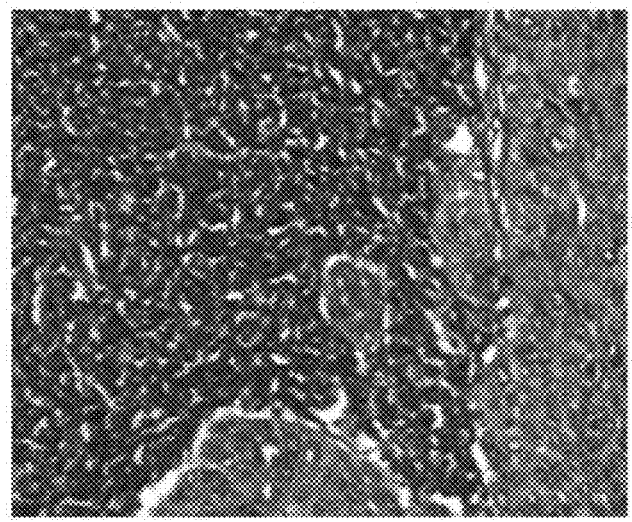
Figure 22B:
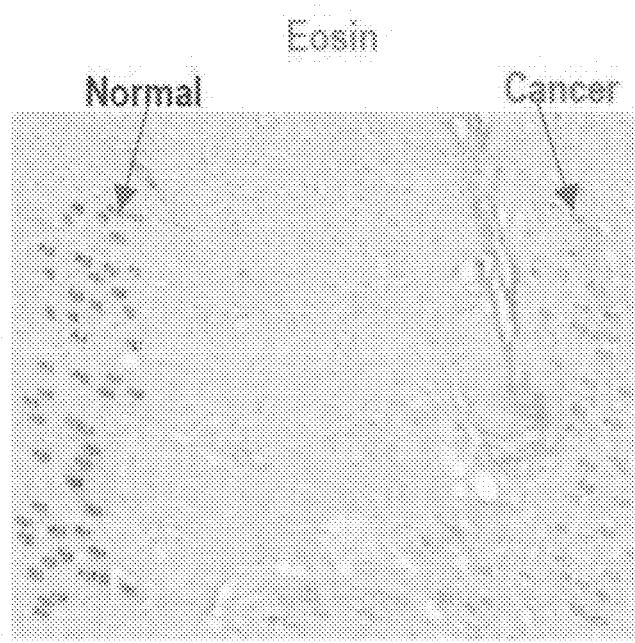
Figure 23E:
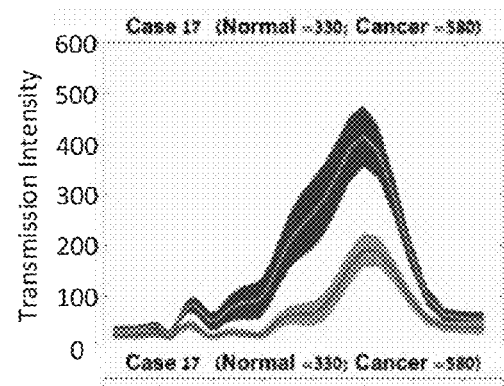
Figure 23E:
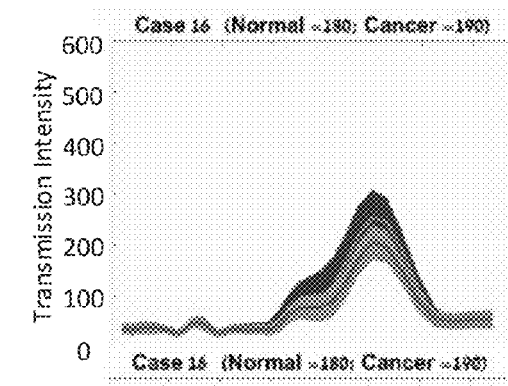
Figure 23F:
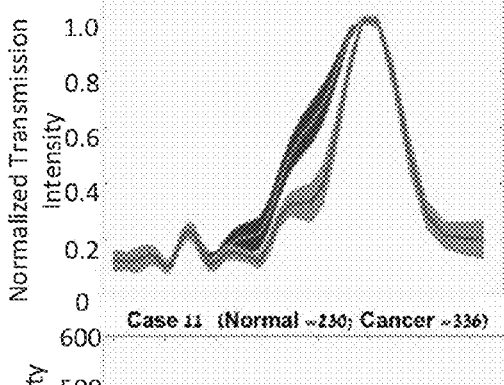
Figure 23F:
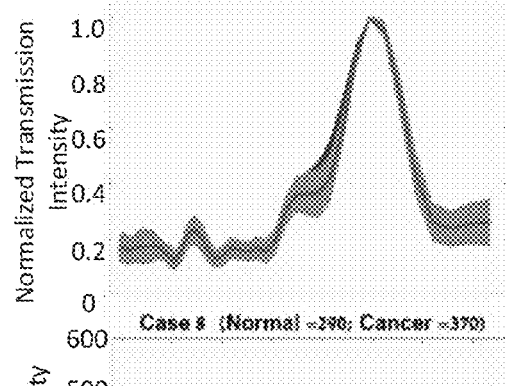
Figure 23G:
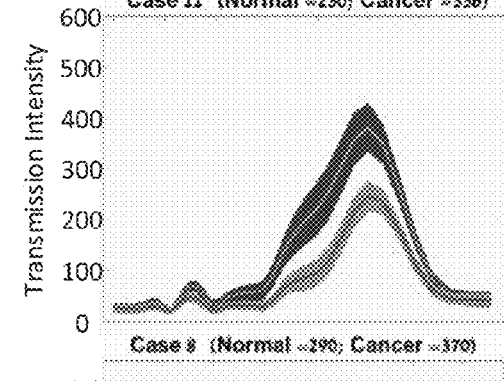
Figure 23G:
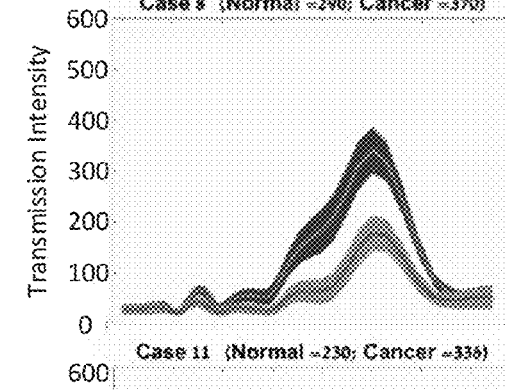
Figure 23H:
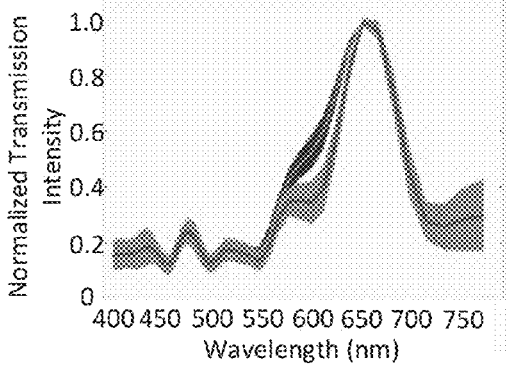
Figure 23H:
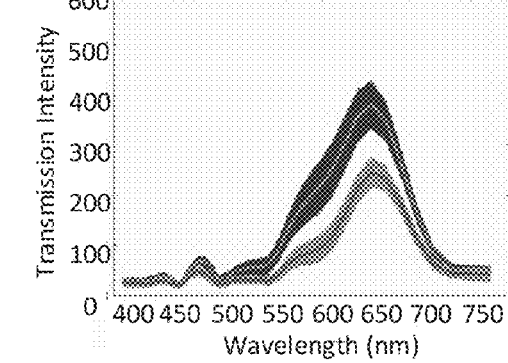
Figure 23I:
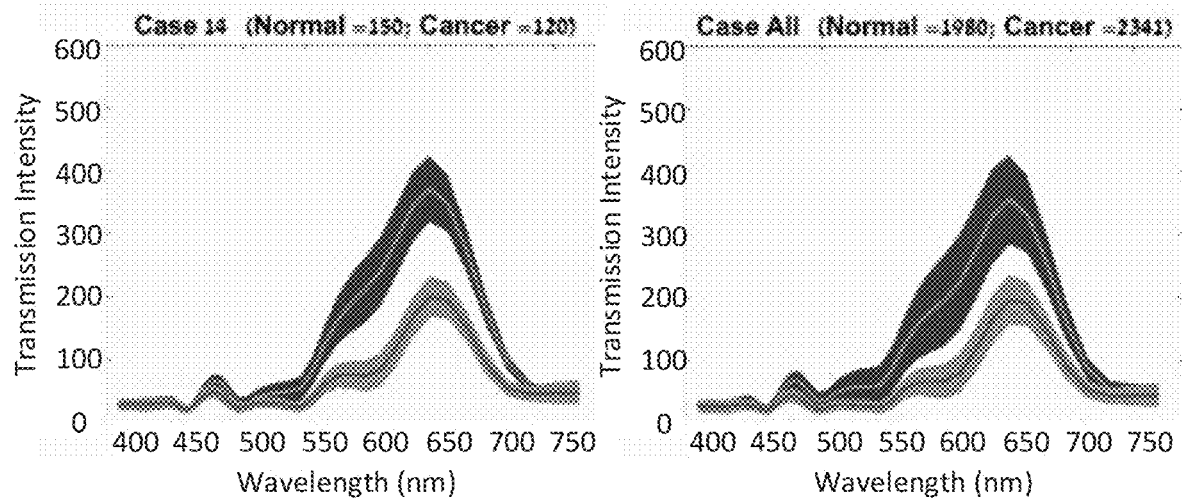
Figure 23J:
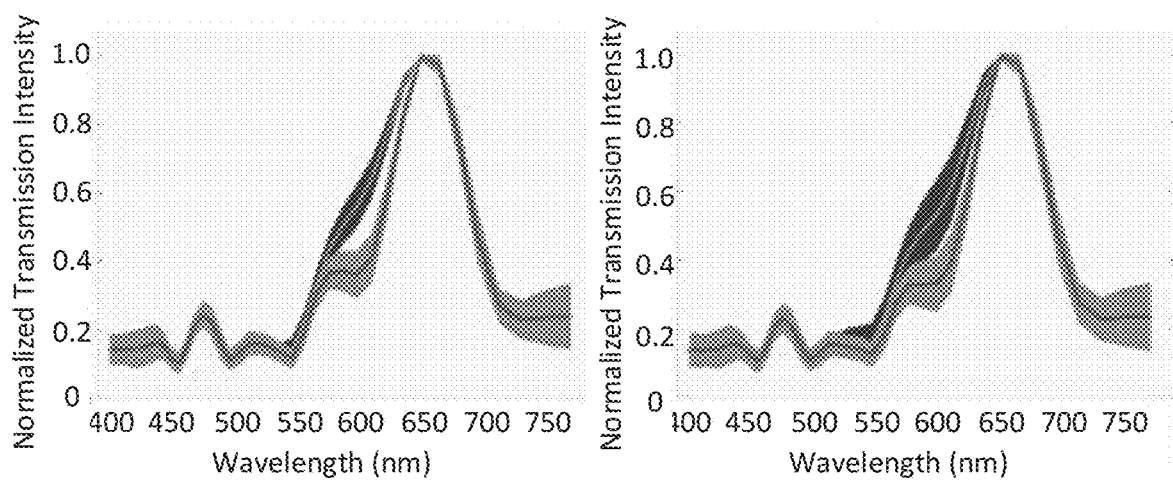
Figure 24:
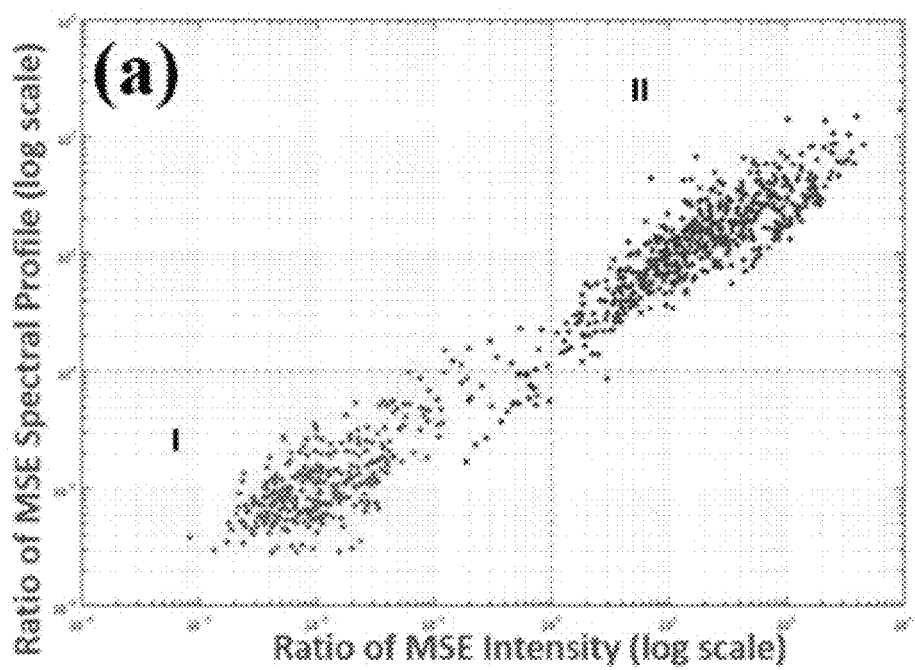
Figure 25:
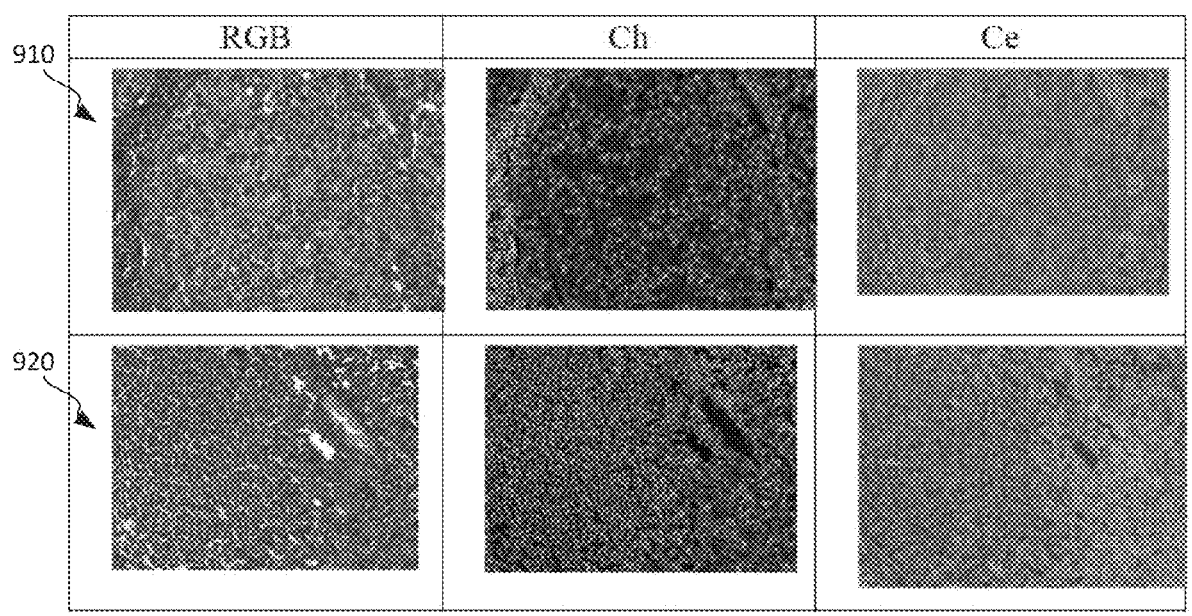

FIGS. 19A, 19B and 19C are a full image of a hematoxylin and eosin stained lymph node tissue section and scanned portions of the section that was scanned based on some embodiments of the present invention;

FIGS. 20A and 20B is a white balanced reconstructed image for a section of one measured biopsy and a zoom-in with marked nuclei respectively, both in accordance with some example embodiments;

FIGS. 21A, 21B, 21C and 21D show example spectra from the experimental results for the biopsy imaged in FIGS. 20A and 20B obtained in accordance with some example embodiments;

FIGS. 22A and 22B show example sections of tissues stained with dyes obtained in accordance with some example embodiments;

FIGS. 23A, 23B, 23C, 23D, 23E, 23F, 23G, 23H, 23I and 23J show mean transmission spectrum and difference in the spectral profile for cancer and normal cells for nine different cases obtained in accordance with some example embodiments;

FIG. 24 is an example scatter plot using a ratio of MSE values for spectral intensity and a ratio of MSE values for spectral shape along the x and y axis respectively; and FIG. 25 shows examples of spectral unmixing in accordance with some example embodiments.

DESCRIPTION OF SPECIFIC EMBODIMENTS OF THE INVENTION

The present invention, in some embodiments thereof, relates to imaging and, more particularly, but not exclusively, to measurement of physical information from an object that is more than the eye can see, such as light polarization and spectrum of a whole image, which can be used, for example, in digital pathology, such as, but not limited to, whole slide imaging.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

According to some example embodiments, the device and method as described herein is based on a leapfrog scanning process configured to provide both rapid scanning and spectral imaging. In some example embodiments, the leapfrog method includes a substantially continuous relative movement between an imager, e.g. a camera and sample being imaged.

The leapfrog method as defined herein refers to a scanning method where each image frame is a two dimensional image of a portion of a sample and consecutive image frames include spatial overlap with a shift of more than one pixel.

Over the scanning duration, the camera is configured to capture image frames at spatial shifts larger than one pixel along the scanning axis. Optionally, the pixel shift between image frames in the scanning direction is in the range of 2-2000 pixels, e.g. 10 pixels, or 100 pixels, or 500 pixels, and is optionally and preferably selected based on system and spectral image requirements. The size of spatial shift may depend on at least one of: size of the sample being imaged, the size of each pixel of the camera, the frame-rate of the camera, the characteristics of the spectrum included, the desired spectral resolution, the spectral character of the features of the sample being measured, the spectral features of the stains used for staining the measured sample, the desired spatial resolution, and the diagnostic method.

Optionally, one or more of the scanning speed and the rate at which the camera captures the images is selectively varied over the scanning procedure, for example to obtain different resolutions over different portions of the sample. In some examples, camera frame rate is set to 100-200 frames/sec, e.g. about 150 frames/sec. The scanning speed may be selected to avoid smearing of the image data. Optionally, the scanning speed is selected to provide less than a one pixel-shift over a duration at which an image is being captured. Optionally, the sample may be illuminated with pulsed illumination, e.g. a strobe light at a controlled frequency. When a strobe light source, or a different mechanism that can turn on or open the light source for short periods of time at high frequency is used, the scanning speed is optionally and preferably increased as compared to scanning with constant illumination.

The ability of the device and method of the present embodiments to gather spectral data from WSI with continuous movement between a camera and sample being imaged is advantageous since it allows increasing the speed at which WSI can be performed, and optionally and preferably also simplifies the mechanical system supporting the imaging as compared to, for example, known stop and go processes. Known stop and go processes require accelerating, decelerating and stopping between image capturing. The Inventors found that this process may be time consuming, require precise mechanical control, and may lead to system vibrations that may harm the system in the long-term.

According to some example embodiments, the method and device employ variations in light characteristics across the image. The variation in light characteristics across the image is optionally and preferably achieved with a variable filter or other light varying element that varies an optical characteristic (or light characteristic). In some example embodiments, the optical element is oriented such that an axis of variation in light characteristics is aligned with the scanning direction.

Representative examples of light varying elements suitable for varying the light characteristics in accordance with some embodiments of the present invention, a linear variable filter, a circular variable filter, a color filter with a number of spectral bands, a liquid crystal variable filter, an acousto-optic variable filter, a prism, a grating, a holographic device and an interferometer is used to vary the illumination across the image.

In some example embodiments, a plurality of light varying elements is aligned parallel to the scanning direction to vary the light characteristics across the image. For example, a linear variable filter and one or more polarization filters may be aligned parallel to the scanning direction. Optionally, there is no need to replace, change or move the light varying elements during the scanning procedure.

According to some example embodiments, an optical system in association with the variable filter or other element for varying the light characteristics is configured to direct light passing through a large part of the working range of the variable filter (or other element) on to an image sensing surface of the camera. As used herein, the large part refers to the spot on the device that originates from a single point of the sample. That spot covers a part of the device that is larger than the smallest point that can be focused optically for a given wavelength, or what is known as the point spread function (PSF) that has a typical dimension as defined by Equation (1):

$$d \approx 1.22\lambda/(2NA) \qquad (1)$$

Where:
λ is the wavelength of light; and
NA is the numerical aperture of the optical setup being used.

For typical green light and large NA=1, this spot is circular with a diameter of about 500 nm. Therefore, a large part of the working range of the variable filter may be a circular, rectangular, square or other shape with a typical dimension that is at least 2-10,000 times larger than the PSF size, as an example, a rectangle of 1 μm×2 mm or 1 mm×1 cm. Optionally, the optical system directs onto the imager light that originates from a single point in the sample and passes through up to at least 10% of an area of the light varying element.

Optionally, the optical system includes a collimating spherical lens at an end proximal to the image plane and a focusing spherical lens proximal to the camera with the variable filter therebetween. Optionally, the focal lengths of the two spherical lenses are matched so that the desired spectral range afforded by the variable filter is imaged on the surface of the camera's imager. Alternatively, a beam-expander is used instead of the focusing spherical lens. The beam-expander, optionally and preferably increases the image size. In these embodiments, optics that de-magnify the image on the camera is used instead of the focusing lens.

In some example embodiments, the optical system further includes a pair of cylindrical lenses on either side of the variable filter. Assuming the light path originates from one point of the sample, the first cylindrical lens may focus that light along a first axis of the variable filter that is the axis of light variation. The second cylindrical lens then projects the light onto the spherical focusing lens proximal to the camera or onto the de-magnifying optics, so that it is also focused on the camera plane. One the other hand, light along the second perpendicular axis of the variable filter having a uniform light characteristic may be spread along that axis, while still being focused by the second cylindrical and spherical lenses so that it is also focused on the camera plane. In overall, the effect of this embodiment is that the light that originates from a point of the sample, turns to a rectangle-like shape on the variable filter device, and it is still focused again on the on the surface of the camera's imager.

Optionally, one or both of the spherical lenses may be intrinsic parts of the fore optics and/or the camera. Optionally, the optical system does not include any moving parts and is static with respect to the camera.

In some example embodiments, the variable filter is moved out of focus so that the light originating from one point of the sample may be spread on the linear variable filter to cover a desired spectral range. Representative examples of such desired spectral range include, without limitation, 5 nm, 10 nm or 1-100 nm. The desired spectral range is optionally and preferably selected so as to reduce the spectral resolution. In this manner less images may be needed to cover the full spectral range being measured albeit with less resolution. Optionally, the spread illumination may then be focused on 1-50 pixels of the camera based on the desired spatial resolution. Optionally, this optical setup and method may be applied when scanning with relatively lower spectral resolution.

According to some example embodiments, spectral data at each point on the sample through a plurality of locations along the variable filter and over a plurality of pixels in the image sensor is collected with the device and method described herein. In this manner, the device and method has substantial immunity to local imperfections that may exist in the variable filter and/or in the image sensing plane and is thereby more robust.

According to some other example embodiments, the light varying element is a time varying element and the scanning is based on coordination between the image capture times and the changes in light characteristics while scanning the sample with respect to the system. Optionally, an entire first frame is captured with a first illumination characteristic, and entire second frame is captured with a second different illumination characteristic with the first frame and the second frame overlapping with a pixel shift greater than 1 pixel, e.g. 3-100 or 10-100 pixels shift. According to some example embodiments, the frame rate of the camera as well as the scan rate is defined so that data for full spectral image and optionally other light characteristics may be gathered despite the shift between frames.

According to some example embodiments, image data accumulated over the scanning duration may be consolidated based on the scanning speed and frame rate of camera to obtain the full spectrum for each pixel of the image, e.g. the spectral image. The information for each pixel may also contain information other than spectral information, such as the polarization properties. A full image or parts thereof may then be stored in a computer readable medium or displayed on a display device, for example, to allow a pathologist for analysis of the sample. Optionally, the image is further processed to provide machine-aided diagnostics or fully automated analysis.

According to some example embodiments, the device includes a handheld fiberscope to collect the spectral data while a user, e.g., a medical profession manually scans a tissue of interest with the fiberscope. Optionally, the tissue of interest is tissue of a patient exposed (or examined) during a medical procedure, such as, but not limited to, an open surgery procedure, or an endoscopic procedure, or a laparoscopic procedure. According to some example embodiments, the device is configured to capture images with a relatively high frame rate in comparison to expected hand movement of the user to provide ample image data collection. For example, the images may be captured at a frame rate of 50-1000 frames/sec. According to some example embodiments, the collected images are registered and the spectral image is constructed with the leapfrog scanning method as described herein.

According to some example embodiments, the handheld device is part of a system that additionally includes a processor with image processing capability, a monitor and a user interface. In some example, the system is suitable for capturing and displaying spectral images of patient tissue during a medical procedure. Optionally, the spectral images assist the medical staff in detecting cancer cells and a border around an area including cancer cells. Optionally, the system may display on a display device areas with missing spectral information and the medical staff may repeat the imaging as needed during the medical procedure. The system can also produce an alert when spectral information is missing. Optionally, the tissue may be stained prior to imaging to increase detectability, e.g. stain may be applied for a few seconds prior to imaging with the handheld device.

According to some example embodiments, the automated method for detecting cell nuclei imaged in a spectral image is configured to recognize a variety of different types of nuclei. Different types of nuclei may include nuclei from both cancerous and non-cancerous (e.g., normal) cells. Optionally, the method is configured to overcome differences in visual characteristics and non-uniformity, e.g., various regions inside a single nucleus which are very similar to parts of the cytoplasm outside the nucleus that may be associated with cancerous nuclei. In some embodiments of the present invention, the method is based on spectral characteristics, morphological characteristics and spatial characteristics.

In some embodiments of the present invention, the identification is based on spectral characteristics but not on morphological and spatial characteristics. In some example embodiments, the method is based on a machine learning algorithm, e.g., clustering, association rule algorithm, feature evaluation algorithm, subset selection algorithm, support vector machine, classification rules, cost-sensitive classifiers, vote algorithm, stacking algorithm, Bayesian network, decision tree, neural networks, Convolution Neural Network (CNN), instance-based algorithm, linear modeling algorithm, k-nearest neighbor (KNN) analysis, ensemble learning algorithm, probabilistic model, graphical model, logistic regression method (including multinomial logistic regression methods), gradient ascent method, singular value decomposition method, and principle component analysis. Optionally, the machine learning algorithm undergoes a training phase in which example points inside and outside the cells are provided by a user. In some example embodiments, input to the machine learning algorithm includes a specific channel of the intensity data associated with a specified dye used to stain the sample. In some example embodiments, when more than one dye is used to stain the sample, intensity data associated with a specified dye is extracted from the measured intensity data based on comparing the measured intensity data with reference data that is specific for the dye of interest. The extracted intensity data is the channel of the intensity data associated with a specified dye.

According to some example embodiments, spectral properties including spectral intensity (e.g., the intensity at each wavelength) and spectral shape (e.g., the shape of the intensity curve as a function of the wavelength) are detected and used for classifying cells in a tissue sample. In some example embodiments, the spectra detected are compared to reference spectra in a defined wavelength range for each classification, e.g., cancerous and non-cancerous (e.g., normal) cells. The reference spectra may be defined from previously saved data and may optionally be refined based on data collected from the tissue sample being analyzed. Optionally, the spectra analyzed as well as the reference spectra include a defined channel of the spectra that is specific to one of a plurality of dyes used for staining a tissue. Optionally, spectra associated specifically with hematoxylin absorption are used for the analysis, e.g., analysis of tissue samples to detect cancer cells.

The parameter associated with spectral intensity may be mean square error of spectral intensity data of the sample and spectral intensity data of the reference for each classification, or the vectorial properties of each of the spectra when represented as a vector in a multi-dimensional space. In some example embodiments, spectral shape is determined based on normalizing the spectral intensity data of both the sample and the reference and comparing the normalized patterns.

Normalization as used herein refers to the process of dividing the intensities measured for all wavelengths by the same value. The value may be as an example the highest intensity found in the spectrum, or the integral sum of intensities of the whole spectrum.

Optionally, the parameters associated with spectral shape are mean square error as calculated by subtracting the values of a normalized spectral intensity data from the values of a normalized reference spectrum, finding the square of values and summing them up for each classification. Similar analysis can be based on comparison of the spectra when it is described as a vector in a multi-dimensional space. In some example embodiments, a first ratio of the parameters associated with spectral intensity is plotted against a second ratio of the parameters associated with spectral shape, to provide a graph, and classification is based on positioning of a point on the graph.

According to some example embodiments, the device and method may be used to develop personalized medicine, e.g. a personalized drug treatment for cancer. In personalized medicine, a drug (or treatment) is tailored to an individual patient or sub-population of patients based on their predicted response. A known method to predict the response is with protein expression profiling. However, the Inventor found that this method is labor intensive. There is a wide variety of proteins that may have the potential of providing and it is often difficult to distinguish between the proteins because of the subtle differences between the coloring of labels used to identify the proteins. Often, only a few proteins are labeled at a time so that each protein may be properly identified and an iterative process is employed.

According to some example embodiments, the spectral data included in the spectral images constructed may provide sufficient information to distinguish between a plurality of labels for identifying different proteins.

The labels are optionally and preferably color-components having different responses to light. Generally, the method can use n types of color-components for labeling the proteins. Both the number (n) and the concentration levels of the color-components may be selected so as to obtain the desired responses to light. For a given n there may be many different combinations of color responses. For n types of color-components and m different levels of concentration, it is possible to achieve $m^n-1$ different responses to light. For example, with n=5 and m=5 there are 3124 different discernable spectra. The number of different combinations is preferably larger than- or equal to the number of the proteins to be identified.

Any type of color-components can be used for labeling the proteins. In one embodiment, the color-components are fluorescent dyes. These embodiments are particularly useful when fluorescence microscopy is used for acquiring the spectral image. In one embodiment, the color-components are chromophores. These embodiments are particularly useful when transmission microscopy is used for acquiring the spectral image.

Optionally, many proteins may be concurrently labeled on a same tissue sample, e.g. 10-200 proteins with different labeling, e.g., using one or more chromophores (for transmission microscopy), or using one or more fluorescent dyes (for fluorescence microscopy). Each of the chromophore or fluorescent dyes provide a different spectrum that may be identified based on analysis of the spectral data even when the colors look similar. In some example embodiments, a same chromophore or fluorescent dye may be used to label proteins that are known to appear in different parts of the cells. For example, a same chromophore may be used to label a nucleus-protein, a cellular protein and a connective-tissue protein. Intensity of expression for each of these proteins may be distinguished based on their spatial location in the cell. As an example, 100 different proteins may be examined with 20-30 different chromophores by taking into account spatial separation between proteins. In some example embodiments, genetic markers may be labeled in a similar manner and look at all together.

Spectral Imaging Device and Method

Figure 1:
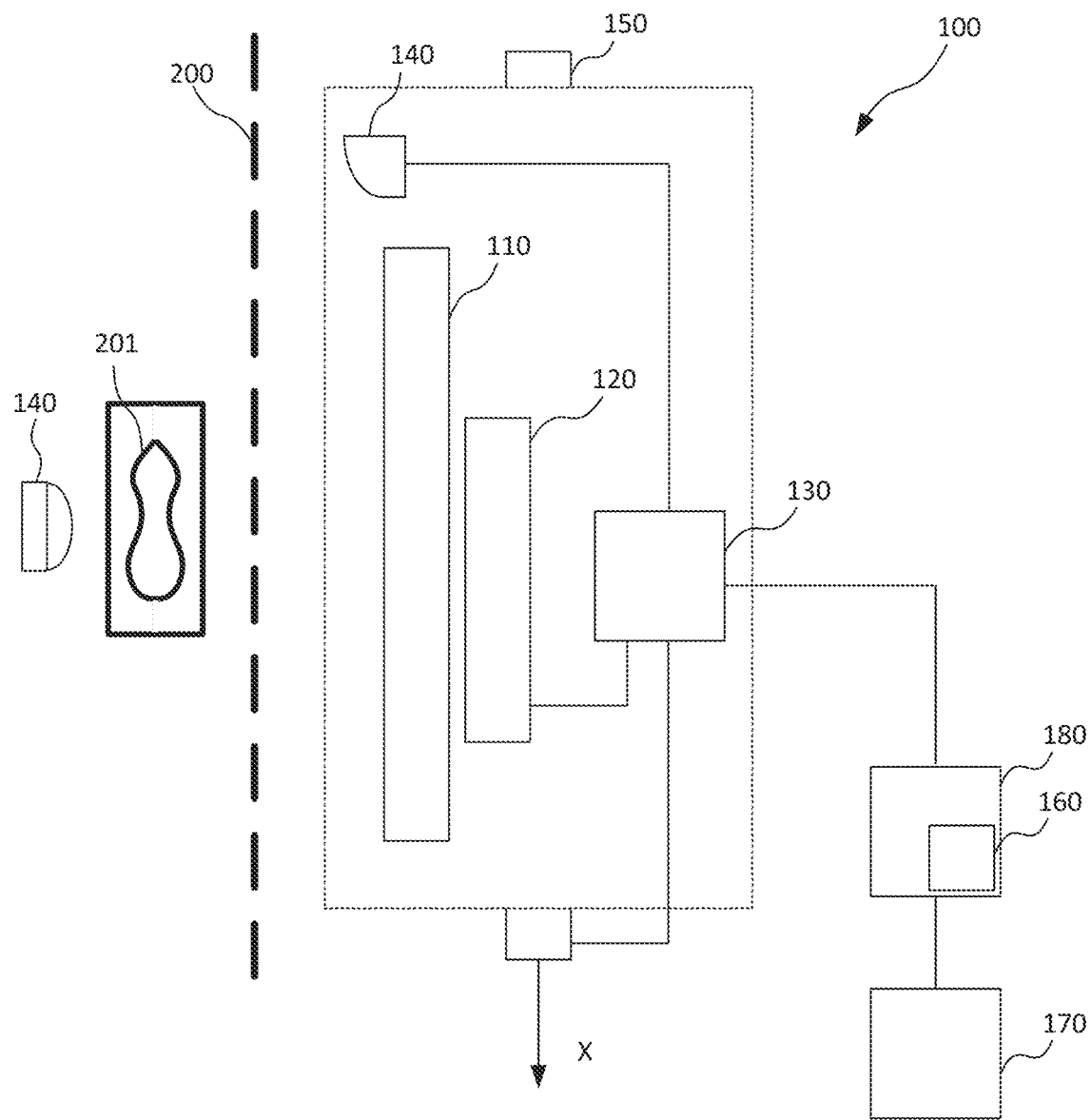

Reference is now made to FIG. 1 showing a simplified block diagram of a spectral imaging device suitable for WSI in accordance with some example embodiments. According to some example embodiments, a spectral imaging device 100 includes an optical system 110, a camera 120 and a controller 130. Controller 130 is configured to control operation of spectral imaging device 100. Camera 120 may be a dedicated camera or an off-the-shelf product, e.g. a CCD or CMOS camera. In some example embodiments, the scanning is performed by device 100 with a linear stage 150 configured to advance device 100 in a scanning direction X and a cross scanning direction Y while a sample 201 to be imaged is stationary. Optionally, scanning stage 150 is configured to advance in scanning direction X at a rate of 0.1-100 mm/sec. In alternate examples, a linear stage may advance sample 201 in a scanning direction and device 100 may be stationary. Optical system is stationary with respect to camera 120. As device 100 advances in the scanning direction with respect to sample 201 and/or image plane 200, camera 120 captures images of sample 201 through optical system 110 at a pre-defined frame rate. The frame rate although pre-defined may be controllably varied over the scanning duration. Optionally, the frame rate of camera 120 is 50-1000 frames/sec. Controller 130 may control operation of camera 120 and linear stage 150 and coordinate their operation.

In some example embodiments, device 100 further includes one or more illumination sources 140 configured to illuminate sample 201. Optionally, a plurality of illumination sources 140 may be spatially spread in device 100 to attain a desired illumination configuration. Optionally, illumination source 140 is positioned on a side of sample 201 that is opposite camera 120. Optionally, illumination source 140 may be configured to illuminate in a plurality of selected bands. Controller 130 may control operation of illumination source(s) 140 in coordination with operation of camera 120. Optionally, spatial dispersion of light is controlled with controller 130 and illumination sources 140 and dispersion element 110 is not required. Optionally, controller 130 is also configured to control, e.g. dynamically control the spectral band at which illumination source(s) illuminates. Optionally, controller 130 is configured to control flashing of illumination source 140 at a defined frequency and over a defined period. Optionally, illumination source 140 is a strobe light. In some alternate embodiments, illumination is external to device 100. Sample 201 may be imaged as is or alternatively through a microscope to obtain a larger image. When using a microscope, device 100 is configured to capture images of image plane 200 exiting from the microscope. Optionally, when using a microscope, illumination source(s) 140 is not required as the microscope has its own illumination. Optionally, controller 130 may be configured to control operation of the microscope, e.g. control illumination with the microscope.

According to some example embodiments, device 100 includes or is associated with a computing device 180 that includes dedicated software and/or firmware 160 for processing image data from camera 120. Computing device 180 may consolidate the image data captured during scanning and create a spectral image(s) from the image data captured. The spectral image or selected portions of the image may be displayed with user interface 170. In some example embodiments, software and/or firmware 160 is additionally configured to further process the image data received and provide machine-aided diagnostics or fully automated analysis. Optionally, computing device with software 180 and/or firmware 160 may be configured to compute one or more parameters related to the image data collected. Optionally, user interface 170 is configured to communicate a report, e.g. display a report based on the performed machine-aided diagnostics or fully automated analysis and/or display the parameters detected. Possibly, firmware 160 contains multiple central processing units (CPU) and/or one more multiple graphics processing unit (GPU) and large and fast memory devices.

Figure 2A:
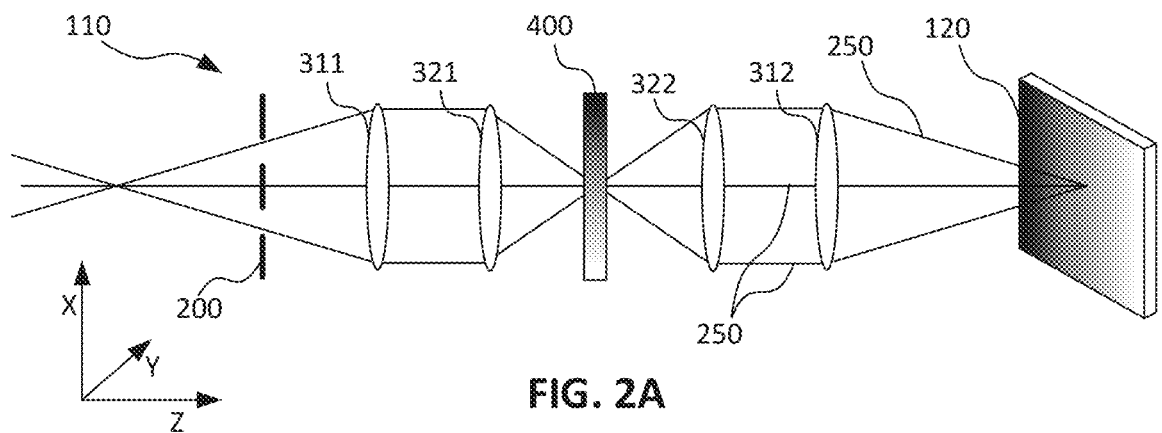
Figure 2B:
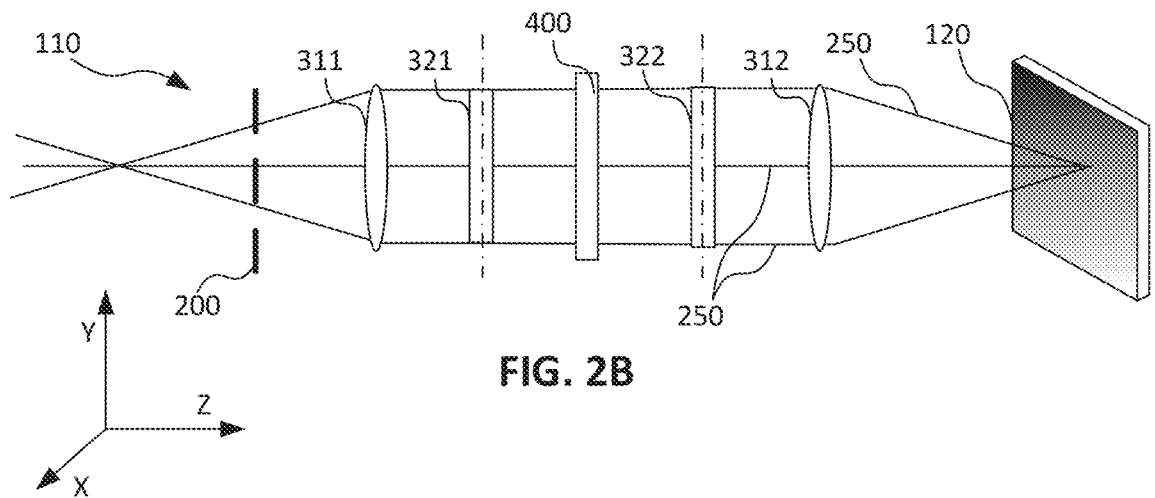

Reference is now made to FIGS. 2A and 2B showing simplified schematic top and side view respectively of an example optical system of the spectral imaging device in accordance with some example embodiments. According to some example embodiments, optical system 110 includes light varying element 400 mounted between at least one pair of lenses. In some example embodiments, light varying element 400 is a variable filter for spectrally varying light. According to some example embodiments, the pair of lenses is configured to spread light rays 250 from a point on image plane 200 along a cross-scan direction Y on light varying element 400 and then gather the spread light rays 250 onto a pixel of camera 120. According to some example embodiments, light varying element 400 is configured to have uniform light characteristics along the cross scan direction, Y. Spreading light rays 250 in the Y direction, provides an averaging effect that may improve the signal to noise (SNR) ratio and reduce false readings due to local imperfections in the light varying element 400 that can lead to defects in spectral information.

In some example embodiments, light varying element 400 is a linearly varying element and optical system 110 includes a pair of cylindrical lenses (including cylindrical lens 321 and 322) on either side of light varying element 400 as well as a pair of spherical lenses (including spherical lens 311 and 312) on either side of pair of cylindrical lens, e.g. sandwiching pair of cylindrical lens. Pair of spherical lenses may include a collimating spherical lens 311 facing image plane 200 and a focusing spherical lens 312 facing camera 120. In some example embodiments, focal lengths of the pair of spherical lenses are matched so that a desired spectral range provided by light varying element 400 is imaged on camera 120. Optionally, the desired spectral range is the entire spectral range of light varying element 400. According to some example embodiments, cylindrical lens 321 is configured to focus light rays 250 along scanning direction X (FIG. 2A) and maintain the collimation along the cross scan direction Y (FIG. 2B). Cylindrical lens 322 may then collimate light rays 250 toward spherical lens 312.

According to some example embodiments, light varying element 400 is configured to spatial vary spectral characteristic of light originating from sample 201 or image plane 200. In some example embodiments, light varying element 400 may be a dedicated element for a specific application, e.g. WSI or an off-the-shelf linearly varying color filter and may optionally be significantly larger than camera 120. One example filter may be an LV-VIS-NIR Bandpass Filter HSI manufactured by Delta Optical Thin Film A/S from Denmark. As an example, the LV-VIS-NIR Bandpass Filter HSI has a size of 25 mm along the variable color axis, a height of 32.5 mm and a thickness of about 1 mm. At each point along its differential axis, this filter is configured to transmit only a narrow spectral-band with a spectral resolution that can be, as an example, 10 nm and in general 1-100 nm. Camera 120 may for example be a CMOS camera manufactured by Lumenera (Ottawa, Ontario, Canada) model Lt225 with dimensions 11 mm×6 mm. Since the example off-the-shelf filter is significantly larger than the example off-the-shelf camera, it is not possible to benefit from the entire spectral range of the filter based on positioning the filter directly on the camera. Instead, according to some example embodiments, optical system 110 is configured to focus light rays 250 so that each image frame captured by camera 120 may cover the whole spectral range, e.g. a desired spectral range along variable color axis of light varying element 400, e.g. along the X axis. Optionally, a final spectral image may include image data for 20-50 spectral bands per pixel, e.g. 40 spectral bands per pixel. Other size and shapes for light varying element 400 may be integrated into optical system 110.

Light varying element 400 may alternatively be a circular variable filter, a color filter with a number of filters each having different spectral transmission parameters, a liquid crystal variable filter, acousto-optic variable filter, a prism, a grating, and a holographic device. In some example embodiments, light varying element 400 is an array of optical elements, each with different optical characteristics. According to some example embodiments, a direction of variation in the light varying element 400 including the array of optical elements is aligned with scanning direction, X.

Figure 3:
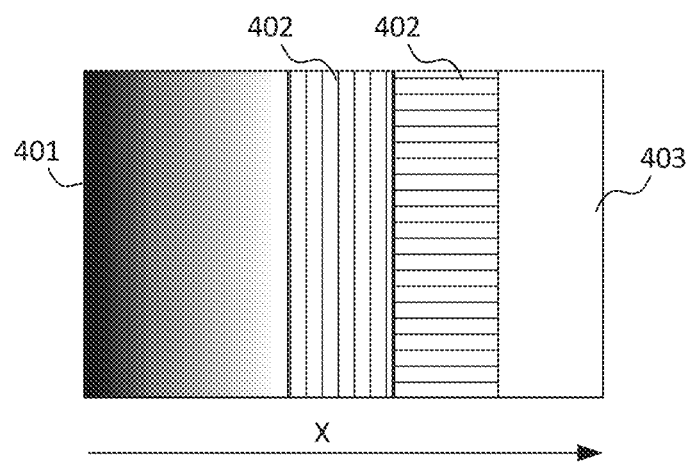

Reference is now made to FIG. 3 showing a schematic representation of example light varying element for the optical system in accordance with some example embodiments. According to some example embodiments, light varying element 400 includes an array of optical elements configured to select spectral properties of light rays 250 penetrating therethrough and optionally reflected therefrom.

Example optical elements may include linear variable filter 401, one or more polarization filters 402 aligned along different directions and transparent element 403. Optionally, transparent element may be configured to detect an overall light intensity. Optionally, image data collected one or more of the optical elements are not applied to construct the spectral image but rather provides additional parameters that may be used to process the image data. In some example embodiments, the additional information collected with for example polarization filters 402 and transparent element 403 may provide additional information related to sample 201 that can be used for further image processing, as well as assisted and/or automated analysis and diagnosis. In some example embodiments, when the device is used for pathological applications, the spectral image may be displayed to the pathologist and may be enhanced based on the additional information detected. Optionally, element 402 may contain two filters that transmit intensity that varies between 0% and 100% at a certain spatial frequency, one along the X axis and the other along the Y axis. The information measured when the sample is scanned along these filters may be used for calculating an image with spatial resolution that is better than a diffraction-limited spatial resolution.

Reference is now made again to FIG. 1. According to some example embodiments, during operation of device 100, optical system 110 with camera 120 is advanced in scanning direction X with respect to sample 201 and/or image plane 200 as camera 120 captures a series of images, each image including a portion of image plane 200. According to some example embodiments, controller 130 (FIG. 1) controls synchronization between image capture rate and scanning speed so that consecutive image frames include overlapping portions of image plane 200. The shift (or leap) in the scanning direction between the overlapping portions may be pre-defined and controlled. Optionally, the defined shift is greater than 1 pixel and may be selected between 3-50 pixels or 3-100 pixels. Optionally, camera 120 captures images at a rate of between 100-200 frames/sec so that there is substantially no smearing due to movement of linear stage 150. Optionally, movement between image plane 200 and camera 120 is less the 1 pixel or less than 2 pixels over a duration of capturing a single image.

Furthermore, the final spectral image is substantially immune to individual pixel defects in camera 120. Since the direction of variation in the light varying element 400 is aligned with scanning direction, X, a same point in image plane is captured with variations in light characteristics in different image frames. In this manner, each point in image plane 200 is captured by a range of pixels in camera 120.

Figure 4A:
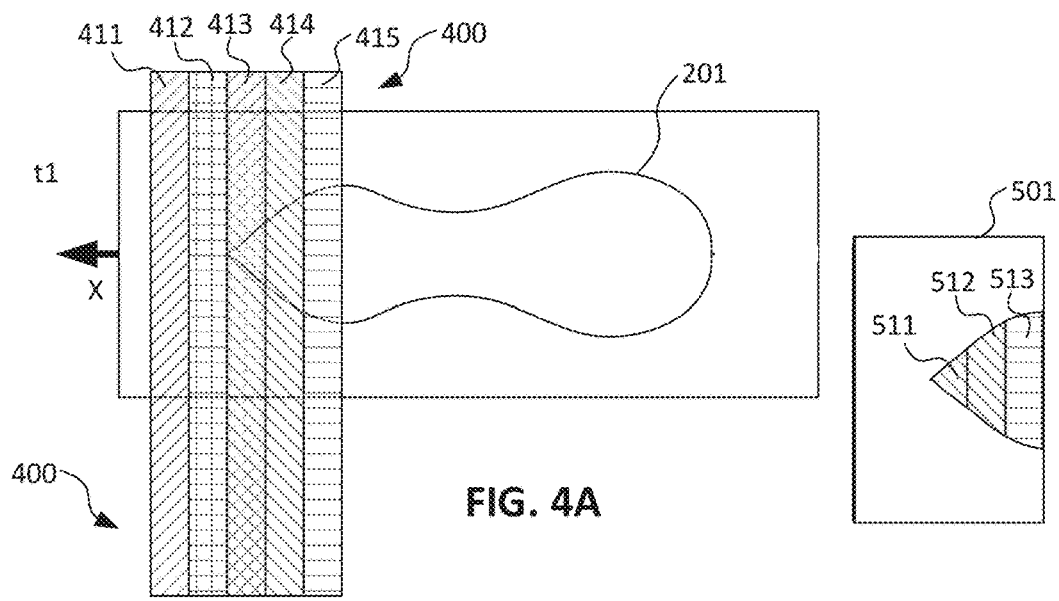
Figure 4B:
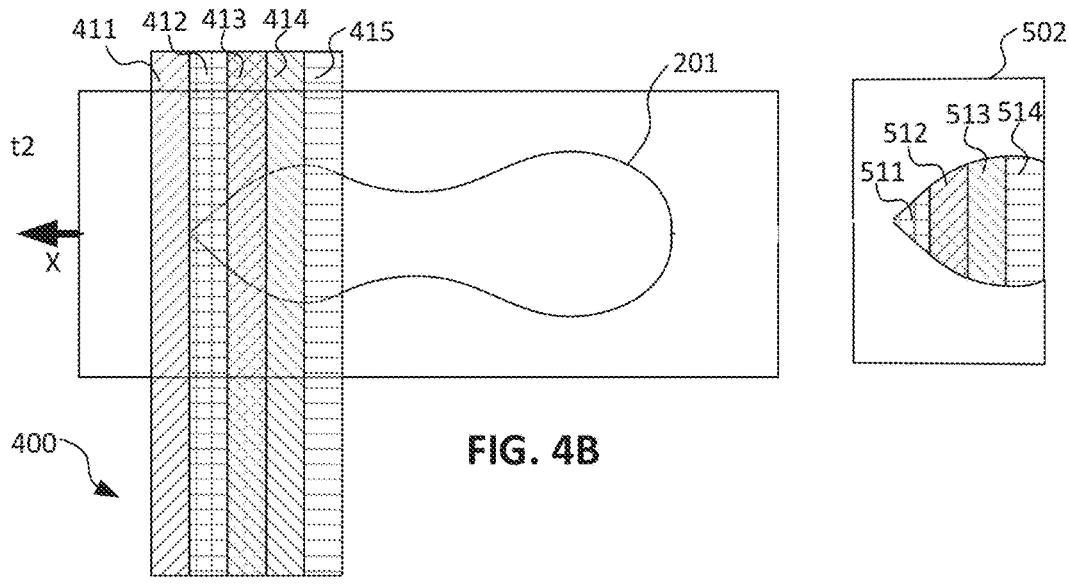
Figure 4C:
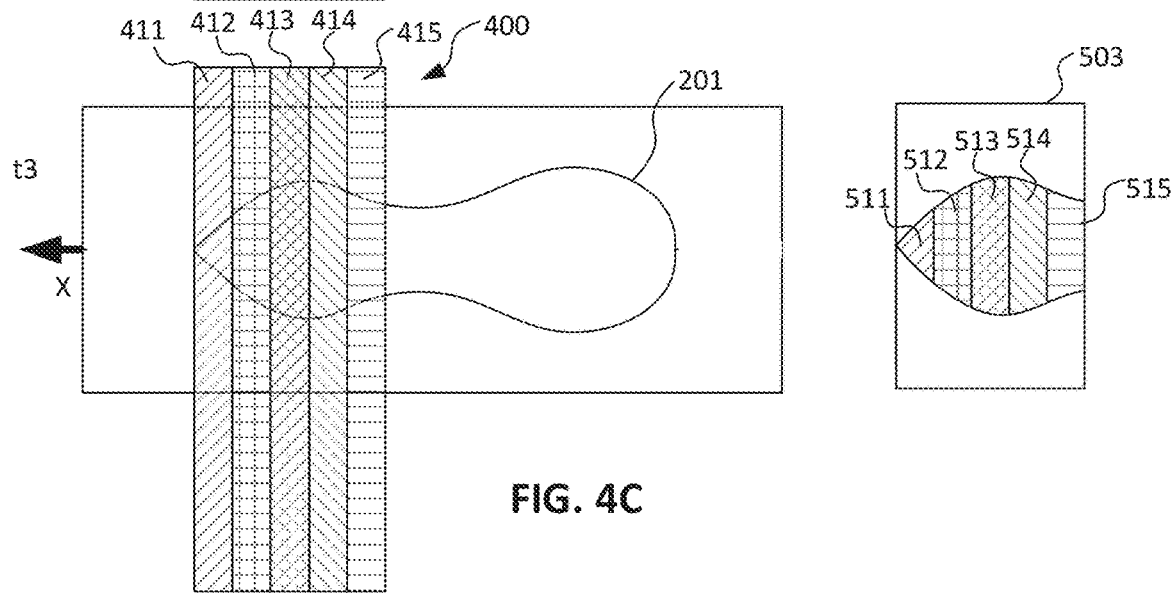

Reference is now made specifically to FIGS. 4A, 4B and 4C showing schematic representations of three consecutive scanning positions and corresponding captured frames all in accordance with some example embodiments. For exemplary purposes, light varying element 400 is shown to include five discrete spectral bands 411, 412, 413, 414 and 415. At time t1, a first image 501 of a portion of sample 201 may as an example include first sub-portion 511 imaged through spectral filtering band 413, second sub-portion 512 imaged through spectral filtering band 414 and third sub-portion 513 imaged through spectral filtering band 415. In a next example consecutive step (time t2), a second image 502 is captured including another portion of sample 201. Image 502 includes first sub-portion 511 imaged through spectral filtering band 412, second sub-portion 512 imaged through spectral filtering ban 413, a third sub-portion 513 imaged through spectral filtering band 414 and also a forth sub-portion 514 imaged through spectral filtering band 415. In third image 503 captured at time t3, first sub-portion 511 is imaged through spectral filtering band 411, second sub-portion 512 imaged through spectral filtering ban 412, third sub-portion 513 imaged through spectral filtering band 413, forth sub-portion 514 imaged through spectral filtering band 414 and a fifth sub-portion 515 imaged through spectral filtering band 515. In this simplified example, each of sub-portions 511, 512 and 513 has been captured in three different spectral bands over three consecutive frames. It is noted that for simplicity, the example shown in FIGS. 4A, 4B and 4C depicts a case when a spatial shift of the image between images captured equals a width of a spectral band. Optionally, the shift may be larger or smaller depending on the desired spectral resolution. As an example, when operating the device with a shift of 30-50 pixels between image frames, a spectral resolution of about 10-15 nm steps, e.g. 30-40 points in the spectral range of 400-800 nm may be obtained in the final spectral image.

Reference is now made to FIGS. 5A and 5B showing a simplified schematic top and side view respectively of an example optical system for measuring spectral images with high spectral resolution that is adapted for measuring relatively low spectral resolution in accordance with some example embodiments. In some example embodiments, a relatively low spectral resolution may be desired to reduce size of the image data required and/or to increase speed of imaging. Low resolution measurement may lead to large shifts of the sample with respect to the optical system and therefore do not cover the full spectral range for all points in the image. In some example embodiments, better coverage may be provided for low resolution imaging based on defocusing the image along scanning direction, X. Optionally, defocusing may be accomplished by shifting light varying element 400 either to the left or to the right while maintaining position of the other optical elements in optical system 110. In the example shown in FIGS. 5A and 5B, light varying element 400 is shifted to the left toward cylindrical lens 321. The shift effects the spread along the scanning direction, X so that a wider band is represented at each pixel in camera 120. The overall effect is that relatively fewer spectral bands may be measured, e.g. larger leaps, and each of the spectral bands measured include relatively more wavelengths, e.g. a wider spectral band, so that there may be no loss of information.

Reference is now made to FIG. 6 showing a simplified schematic representation of another example optical system for spectral imaging that is suitable for WSI in accordance with some example embodiments. According to some example embodiments, optical system 110' includes a prism or grating as light varying element 400'. Light varying element 400' may receive light rays 250 from imaging plane 200, divide light rays 250 into different spectral bands or wavelengths, e.g. 251, 252 and 254 and direct each of the spectral bands at a different angle. A collimating lens 730 may collimate illumination from image plane 200 onto light varying element 400 and a focusing lens 740 focuses each of the spectral bands along a line on camera 120 that is parallel to the cross scan direction Y. For example, wavelength 251 may be imaged over line 751. Similarly, wavelength 252 may be imaged over line 752 and wavelength 253 may be imaged over line 753. Over the scanning procedures image data from the different wavelengths may be gathered and consolidated to form a spectral image of image plane 200 (or sample 201). In this setup, however, the wavelengths (e.g. 754 and 752) are intermixed with other wavelengths that originate from different points of the sample that are along the Y axis. To overcome that, the collection of points being measured for all pixels at all different frames may be decomposed by a de-convolution algorithm that takes into account the wavelength-spatial intermixing parameters.

Reference is now made to FIG. 7 showing a simplified schematic representation of time varying optical system for a spectral imaging system suitable for WSI in accordance with some example embodiments. In some example embodiments, an optical system 110 is based on time varying color filter 700 as opposed to a spatially varying color filter 400 as shown for example in FIGS. 2A and 2B. Filter 700 may be for example a liquid crystal tunable filter (LCTF) or an acousto-optic tunable filter (AOTF). Wavelength may be tuned over the duration of the scanning with controller 130 based on tuning the voltage for an LCTF or a frequency for an AOTF. According to some example embodiments, optical system 110" includes a pair of spherical lenses (spherical lens 705 and 710). Spherical lens 705 may be configured to collimate illumination from image plane 200 and spherical lens 710 may be configured to focus illumination on to camera 120. According to some example embodiments, controller 130 alters voltage or frequency in synchronization with the scan speed (on the fly), so that the image of every point of the sample is imaged by a series of pixels along the scanning axis X of the camera 120. As the transmitted wavelength is controllably changed (based on changing voltage or frequency), each point in image plane 200 is measured with a different wavelength. At the end of the scanning procedures, image data is consolidated to form the spectral image(s). The wavelengths in each frame are known based on the input voltage or frequency.

FIG. 8 is a simplified flow chart of an example method for spectral imaging that is suitable for WSI in accordance with some example embodiments. According to some example embodiments, different scanning parameters may be defined for different applications (block 610). Optionally, the requirements may be provided by a user through a user interface 170 and may be based on a desired resolution and/or based on a desired speed for completing the imaging process. Optionally, the parameters defined are one or more of the image capture rate (frames/sec) and the scanning speed. Once the parameters are defined, the image data may be collected (block 620). According to some example embodiments, the image data may be collected by the device without human intervention. Image data collected may be consolidated based on the known scanning speed and image capture rate to construct the spectral image (block 630). The spectral image may then be displayed to a user on a display (block 640). In some example embodiments, the spectral image may be further processed to provide machine-aided diagnostics and/or automated analysis (block 650). Output from the processing may be reported to the user via the user interface (block 660). Optionally, the spectral image may be further processed to provide machine-aided diagnostics and/or automated analysis (block 650) and the output may be displayed to the user together with the spectral image.

Method for Automated Detection of Nuclei in a Sample

According to some example embodiments, automated detection of nuclei in a stained tissue sample is based on a machine learning process that receives spectral image data of the stained tissue sample and identifies nuclei in the sample based on its spectral characteristics. In some example embodiments, the machine learning engine is pre-trained.

In some example embodiments, the spectral image is an image of a tissue sample that has been stained with two or more dyes. Optionally, the tissue sample has been stained by hematoxylin and eosin dyes. In some example embodiments, during the automated detection process, the spectral image is pre-processed to separate spectral data from each of the different dyes, e.g. hematoxylin and eosin dyes in the received image and determine dye concentrations at each pixel.

According to some example embodiments, hematoxylin and eosin concentrations at each pixel may be computed with Equation (2):

$$\begin{matrix} C_H \\ C_E \end{matrix} = F_{LI^*} \begin{bmatrix} A(\lambda 1) \\ \vdots \\ A(\lambda m) \end{bmatrix} \quad (2)$$

Where:
$\lambda_i$, i=1, ..., M are the acquisition wavelengths (e.g. M=40);
$A(\lambda i)$, are the absorption values per wavelength,
$F_{LI}$ is a left-side inverse of a matrix F including reference spectra for each dye, and
$C_H$, $C_E$ are the concentrations of hematoxylin and eosin respectively.

Optionally, the image received is an image of transmitted light. Absorption may be computed from the measured transmitted light based on Equation (3):

$$A(\lambda) = -\log \frac{I(\lambda)}{I_0(\lambda)} \quad (3)$$

Where:
$I(\lambda)$ is intensity of light at the acquisition wavelengths as detected in the image,
$I_0(\lambda)$ is the spectrum of the light source, and
$A(\lambda)$ is the corresponding absorbance of the tissue sample at the acquisition wavelengths.

In some example embodiments, matrix F is determined by separately scanning the pure dyes in DMSO (Dimethyl sulfoxide) solution, using the same imaging conditions and protocol as was used for the acquisition of the images. An example of reference spectra for hematoxylin is shown in FIG. 12A and an example of reference spectra for eosin is shown in FIG. 12B. Optionally, each column in matrix F includes the spectra from one of the dyes.

Using Equation (2), an H-channel (Ch) representing absorbance associated with hematoxylin and an E-channel (Ce) representing absorbance associated with eosin may be determined for each pixel of the image.

Reference is now made to FIG. 9 showing a simplified flow chart of an example method to train a nuclei detection engine in accordance with some example embodiments. A training spectral image, e.g. a spectral image acquired based on the device and methods described herein, may be acquired and provided to a nuclei detection engine. In some example embodiments, the nuclei detection engine displays the image (block 705) and multiple locations inside and outside of nuclei are manually provided by a user (a pathologist) and the marked locations are received by the training algorithm (block 710). Sample patches around each of the locations indicated may be extracted from the image based on a segmentation process (block 715). The segmentation process may automatically segment the nuclei based on intensity and spectral data. Optionally, the patches may include 16×16 pixels or a square of pixels include 5-50 pixels in each dimension. Optionally, one or more of the patches are rotated in a plurality of orientations to provide additional input to the training algorithm.

According to some example embodiments, normalized spectral data is computed for each of the patches (block 720). Optionally, the spectral data is the intensity values of the spectra per pixel. Optionally, the spectra may be selected as an average spectrum from the whole area of each nucleus, as determined by segmentation process. In some example embodiments, when more than one dye is used to stain the sample, e.g. hematoxylin and eosin, the spectral data provided includes spectral data specifically from one of the channels, e.g. H-channel (Ch). Optionally, the input is normalized. According to some example embodiments, the nuclei detection engine is trained based on the spectral data provided (block 725). Optionally, the nuclei detection engine is operated based on machine learning algorithms, e.g. a Convolutional Neural Network (CNN) algorithm.

Reference is now made to FIG. 10 showing a simplified flow chart of an example method to identify nuclei in a sample with automated nuclei detection engine in accordance with some example embodiments. According to some example embodiments, a nuclei detection engine is configured to receive spectral images (block 750). Optionally the spectral images are captured based on the device and methods described herein. In some example embodiments, spectral data is separated into channels associated with each of the dyes, e.g. Ch and Ce (block 755). Spectral data, e.g. intensity values for each channel may be normalized (block 760). Optionally, patches are extracted around each of a plurality of pixels based on the normalized spectral data (block 765). Optionally, a specific channel, e.g. Ch may be applied for extracting the patches. Each patch may be classified as either being a nucleus or not being a nucleus based on the machine learning algorithm (block 770) and a label may be assigned to a central pixel of each patch (block 775). According to some example embodiments, the labeled pixels may be displayed and/or may be input to an algorithm configured to classify the nuclei into one or more groups, e.g. cancerous and normal nuclei. Although, embodiments related to identifying and classifying nuclei are discussed herein, it is noted that a similar method may be applied to identify and classify other elements such as whole cells, various types of connective tissue, extracellular matrix, fibers, epithelium, dermis, and various glands.

Spectral Differentiation of Cells in a Sample

The present inventors have found nuclei of cancer and normal cells stained in hematoxylin and eosin showed significant differences in both amplitude spectral intensity and shape of the spectral intensity across the wavelength band. This difference was found when comparing health lymph nodes in the breast with cancerous lymph nodes. Similar results were found for colon cancer cells. Reference is now made to FIGS. 11A and 11B shown example graphs comparing measured transmission spectra and normalized transmission spectra respectively for normal and cancer nuclei in accordance with some example embodiments. The example graphs compare average values of 150 normal nuclei with average values of 120 cancer nuclei. The average values and standard deviations are shown for both normal and cancer cells. High intensity values for cancer cells were found in wavelengths between 550 nm-700 nm. Furthermore, a distinct shoulder between 550 nm-600 nm was found in spectrum for normal nuclei but not for cancer nuclei. The distinction in shape is further clarified when normalizing the transmission spectra for both normal and cancer cells as shown in FIG. 11B. According to some example embodiments, both spectral intensity and spectral shape of a nucleus in a sample is determined and used to classify the nucleus.

FIGS. 12A, 12B, 12C are absorption spectra of normal and cancer nuclei for dye specific channels in accordance with some example embodiments. FIG. 12A shows an example absorption of nuclei stained only with Hematoxylin in cancer cells (green) and normal cells (red). FIG. 12B shows example absorption of nuclei stained only with Eosin from normal and cancer cells. FIG. 12C shows the spectrum measured in normal and cancer cells stained with both Hematoxylin and Eosin. The absorption values were determined based on Equation (3). In FIG. 12B Eosin can be seen to have significantly weaker absorbance as compared to Hematoxylin. Based on FIG. 12A it is clear that in this example the normal cells had a higher absorption in general, but more specifically the difference peaked around 600 nm. In some example embodiments, the differences and spectral characteristics may be determined in defined wavelength bands that are specific to the dye being used for staining the tissue. Furthermore, in some example embodiments, the spectral characteristics may be determined from computed spectral channel for a specific dye when more than one dye is used.

Reference is now made to FIG. 13 showing a simplified flow chart of an example method for classifying nuclei based on spectral intensity and spectral shape in accordance with some example embodiments. According to some example embodiments, a spectral image of a tissue sample is acquired (block 805). The tissue sample may be stained with one or more dyes prior to imaging. Optionally, the tissue is lymph nodes from a human breast. Optionally, the tissue is stained with hematoxylin and eosin. Optionally, spectral image acquisition is based on the device and method described herein. Alternatively, spectral images may be acquired by known spectral imaging techniques.

According to some example embodiments, nuclei are identified in the spectral images (block 810). Nuclei identification may be performed based on an automated algorithm as described herein or may be manually selected. Optionally, a combination of automated and manual selection and/or verification is performed.

According to some example embodiments, the spectral image is analyzed to determine intensity due to nuclei absorption over the spectra (block 815). Optionally, intensity is determined over a defined wavelength band of interest. Optionally, the spectral image intensity is divided into specified channels, each channel associated with one of the dyes used to stain the sample and the intensity is detected over one or more of the channels. Optionally, intensity of an H-channel (Ch) is detected. Optionally, the intensity detected is average intensity across the defined wavelength band.

According to some example embodiments, the intensity (or average intensity) is compared with corresponding reference values for each of the different defined classification of the cells (block 820). In some example embodiments, a mean square error (MSE) between the intensity and each of the reference intensities is computed. Optionally, the defined classifications include cancer cells and normal cells. The reference values may optionally be included in a table stored in memory that is accessible to the automated classification engine. Optionally, the reference values are updated or refined over the classification procedure based on spectral data of the tissue being analyzed.

According to some example embodiments, the spectral image is analyzed to determine intensity shape due to nuclei absorption over the spectra (block 825). Optionally, shape of intensity is determined over a defined wavelength band of interest. Optionally, the spectral image intensity is divided into specified channels, each channel associated with one of the dyes used to stain the sample and the intensity shape is detected over one or more of the channels. Optionally, intensity shape of an H-channel (Ch) is detected. According to some example embodiments, the shape is quantified based on normalizing intensity levels over the selected wavelength band.

According to some example embodiments, the normalized intensity is compared with corresponding reference values for each of the different defined classification of the cells (block 830). In some example embodiments, a mean square error (MSE) between the normalized intensity and each of the reference normalized intensities is computed. The average or summation may characterize the differences in shape. Optionally, the defined classifications include cancer cells and normal cells. The reference values may optionally be included in a table stored in memory that is accessible to the automated classification engine. Optionally, the reference values are updated or refined over the classification procedure based on spectral data of the tissue being analyzed. The MSEs between the sample spectrum and each of the reference spectra is computed and may be defined by the following Equations (4):

$$MSE = \int_{\lambda_1}^{\lambda_2} (I_\lambda - I_{\lambda,REF})^2 d\lambda \quad (4)$$

Similar MSEs may be calculated when taking the normalized tested spectrum and each one of the normalized reference spectra. According to some example embodiments, the identified nuclei are classified based on the comparison, e.g. the MSEs computed (block 835). In some example embodiments, a ratio of MSE values are computed and used for classification. The ratios may be defined by the following equations:

$$I_1 = \frac{\int_{\lambda_1}^{\lambda_2}(I_\lambda - I_{\lambda,RN})^2 d\lambda}{\int_{\lambda_1}^{\lambda_2}(I_\lambda - I_{\lambda,RC})^2 d\lambda}; \quad I_2 = \frac{\int_{\lambda_1}^{\lambda_2}(\hat{I}_\lambda - \hat{I}_{\lambda,RN})^2 d\lambda}{\int_{\lambda_1}^{\lambda_2}(\hat{I}_\lambda - \hat{I}_{\lambda,RC})^2 d\lambda} \quad (5)$$

Where:
$I_1$ is the MSE ratio for spectral intensity,
$I_2$ is the MSE ratio for spectral shape,
$I_\lambda$ is the spectral intensity,
$I_{\lambda,RN}$ is the reference spectral intensity for a first classification (e.g. normal cells),
$I_{\lambda,RC}$ is the reference spectral intensity for a second classification (e.g. cancerous cells),
$\hat{I}_\lambda$ is the normalized spectral intensity,
$\hat{I}_{\lambda,RN}$ is the reference normalized spectral intensity for a first classification (e.g. normal cells), and
$\hat{I}_{\lambda,RC}$ is the reference normalized spectral intensity for a second classification (e.g. cancerous cells).

The results may be reported (block 837), e.g. may be displayed on a computer screen.

Reference is now made to FIG. 14 showing an example classification scheme for differentiating between cancer and normal cells in accordance with some example embodiments. In some example embodiments, samples that fall within Zone 1 may be classified as normal, samples that fall within Zone 3 may be classified as cancer cells.

Both ratios may be used for classification. For example, when the classification is normal or cancel cells, if the spectrum of a tested nucleus is more similar to that of a normal cell, then the numerator for both parameters should be rather small, and the denominator should be larger. Furthermore, for a normal cell, both $I_1$ and $I_2$ values should be smaller than 1 and for cancer cells both parameters should be larger than 1. Optionally, samples that fall within Zone 2 and Zone 4 may be reported for additional analysis. Optionally, samples that fall within Zone 2 and Zone 4 may be further inspected by automated analysis based on additional parameters. As an example, these points may be classified according to their geometric distance to the center of gravity of all points in Zones 1 and 3. Furthermore, the separation to Zones may be performed by splitting the zones through the axes $I_1=1$ and $I_2=1$. An example scatter plot of the ratios of MSE of known samples of cancerous and normal nuclei is shown in FIG. 25 of the examples.

The classification algorithms can include other algorithms that take additional spectral imaging information into account, including algorithms that are based on partial spectral range, artificial intelligence and deep learning algorithms and more. In some example embodiments, parameters that characterize morphology may also be included as an additional parameter for classifying the nuclei. In some example embodiments, based on segmentation of the spectral image to detect the nuclei, other parameters can be considered for classification, such as the size of the nuclei, the sphericity, roughness, granulation, orientation, connection to neighboring cells and more.

Reference is now made to FIG. 15 showing simplified schematic representation of an example spectral imaging acquisition system including a cell classification engine in accordance with some example embodiments. According to some example embodiments, a cell classification engine as described herein is configured to classify cells in a tissue sample over an automated or semi-automated process. The cell classification engine 850 may receive sample spectral images from a spectral imaging acquisition device 851. Optionally, the spectral imaging acquisition device 851 is device 100 (FIG. 1). In some example embodiments, a dedicated nuclei identification engine 852 is configured to identify pixels belonging to nuclei in the sample. Optionally, nuclei identification engine 852 may provide identification in an automated process or semi-automated process. Optionally, the nuclei identification engine as described herein may be used. In some example embodiments, nuclei identification engine 852 provides input to cell classification engine 850. Optionally, user input 853 for identifying or assisting in the identification of nuclei may be received via a user interface device 855. According to some example embodiments, cell classification engine 850 computes spectral parameters and compares the spectral parameters to reference values stored in memory 854. Optionally, additional reference values are accumulated over the classification process and memory 854 may be updated. Output from the classification engine may be reported via user interface device 855.

Reference is now made to FIG. 16A showing a schematic drawing of an example spectral imaging acquisition system including a fiberscope in accordance with some example embodiments. According to some example embodiments, a spectral imaging acquisition system 880 includes a fiberscope 890 that can be used by a medical personnel 865 to manually scan tissue 875 of patient 870 during a medical procedure. In some example embodiments, medical personnel 865 moves fiberscope 890 over the relevant tissue 875. For example, medical personnel 865 may be instructed to move fiberscope 890 in a sliding motion, e.g. from left to right while a camera in system 880 captures images. Tissue 875 may be tissue that is exposed in a surgical procedure and/or may be tissue that is imaged during an endoscopic procedure, laparoscopy procedure or other minimally invasive procedure. According to some example embodiments, system 880 captures images as tissue 875 is manually scanned and constructs a spectral image. The spectral image may be displayed on monitor 885 and medical personnel 865 may inspect the spectral image during the medical procedure. Optionally, medical personnel 865 may first stain tissue 875, e.g. with hematoxylin, let tissue 875 absorb the stain and subsequently perform the imaging.

Reference is now made to FIG. 16B showing a simplified flow chart of an example method for constructing a spectral image with free hand scanning in accordance with some example embodiments. According to some example embodiments, images of tissue may captured at a defined frame rate during free hand scanning of a user (block 806). According to some example embodiments, an image processing engine or processor may perform image registration to detect overlap between consecutive images captured during the scanning and to correct for drift (block 806). Optionally, the registration includes both linear shifting and rotation. A wavelength with which each image was captured may be identified (block 826). According to some example embodiments, based on the registration and the identified wavelengths, a spectral image is constructed using a leapfrog method as described herein (block 836). The spectral image may be displayed to the user as well as to others (block 846). Optionally, portions of the image that may be missing spectral data may be indicated to the user (block 856). Based on this indication, the user may decide to scan the tissue or a portion of the tissue again.

Reference is now made to FIG. 17 showing a simplified flow chart of an example method to perform protein expressions analysis for cancer treatment in accordance with some example embodiments. According to some example embodiments, the spectral images constructed based on the device and method as described herein may be useful for developing personalized medicine. According to some example embodiments, cells in a sample tissue may be stained (block 905). The cells may be stained for example with hematoxylin and/or eosin. According to some example embodiments, each of a plurality of selected proteins are labeled (block 915). Labeling may be with different chromophore (for transmission microscopy) or fluorescent dye (for fluorescence microscopy). Optionally, a same label may be used to label proteins that appear in different spatial locations in the cell. According to some example embodiments, a spectral image is captured with the device and method as described herein (block 925). The spectral image may be inspected and/or analyzed to identify and/or differentiate between cancer cells and healthy cells (block 935). The protein expressions may be evaluated in cancer cells as well as in healthy cells (block 945). According to some example embodiments, expression of a plurality of different proteins may be evaluated in a same tissue sample. According to some example embodiments, the spectral data collected may be decomposed or unmixed with spectral imaging algorithms to identify the different proteins labeled. According to some example embodiments, correlations between an intensity of expression of proteins in each cell that is cancer or healthy may be performed (block 955). According to some example embodiments, blocks 905-955 may be repeated for different scenarios (block 965). For example, the protein expression profile may be evaluated in tissue in which an administered drug was successful in providing a desired outcome as well as in tissue in which an administered drug was not successful in providing a desired outcome. The outcomes may be compared and the protein expressions related to a desirable scenario may be identified (block 975). Optionally, morphological data from the sample may also be evaluated when determining a correlation between intensity of protein expressions and an obtained desired outcome.

It is noted that although, many of the examples described refer to cancer detection, similar analysis may be used for other classifications and/or detections such as for detection of infection, vitality and other parameters. It is also noted that other parameters can be detected by using the spectral image information based on the device and method described herein. This information may be, as an example, the cell type, such as atypical, carcinoma, sarcoma, lymphoma and leukemia, as well as predictive parameters such as tumor stage, and prognostics parameters such as tumor grade.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

Various embodiments and aspects of the present invention as delineated hereinabove and as claimed in the claims section below find experimental support in the following example.

EXAMPLES

Reference is now made to the following example, which together with the above descriptions illustrates some embodiments of the invention in a non limiting fashion.

All the histological sections were cut at 2.5 μm thickness and stained automatically (LEICA ST5020) with the conventional hematoxylin and eosin stain method. The coverslips were also applied automatically (LEICA ST5020). These slides are scanned using VENTANA iScan HT. VENTANA Virtuoso images were analyzed by a pathologist to identify tumor and normal cells. All necessary information related to cancer and normal cells is marked over the scrutinized images.

The necessary 'gold standard' information regarding location of cancer and normal area on the slides was provided by pathologists.

Example 1

A tissue section from a lymph node biopsy was stained with hematoxylin and eosin and the sample was measured with the rapid spectral imaging system based on interferometer. FIG. 18 shows a small part of the spectral image that is 5000×6000 pixels wide. Such an image cannot be measured by a single frame of the camera, and it therefore demonstrates the ability to scan a sample that is significantly larger than the area of the camera. Here, a CMOS camera was used from Lumenera (Ottawa, Ontario, Canada) model Lt225 with dimensions of 11 mm×6 mm and a pixel size of 5.5 μm×5.5 μm and 2048×1088 pixels. The scanner was set to scan at a speed of approximately 0.6 mm/sec and the camera measured at a frame rate of 150 frames/sec. With these parameters it took approximately 5 minutes to scan a 1×1 cm square biopsy that gives 40 points in the spectral range of 400-800 nm. The complete biopsy image is approximately 50,000×37,000 pixels large.

Example 2

FIG. 19A shows a hematoxylin and eosin stained lymph node tissue section for breast cancer diagnosis having a size of about 2000 μm×2000 μm (marked with blue colored box) measured with a 20× objective lens based on some embodiments of the present invention. FIG. 19B shows a reconstructed white-balanced RGB image having a size of about 7400×7616 pixels with 40 spectral channels per pixel. FIG. 19C shows an image after zooming-in on the reconstructed RGB image. A constant moving speed was maintained for each strip of the sample. The sample had a size of 10 mm×0.5 mm. FIGS. 19B and 19C show a portion of a spectral image acquired. The spectral image acquired included 2.2 billion intensity pixels with 40 spectral channels per pixel.

Example 3

Several sections having size of about 300 μm×400 μm (reconstructed image having 1087×1483 pixels with 40 spectral channels) were measured for one example case to determine their significance for diagnosis. A white balanced reconstructed image for a section of Case 14 is shown in FIG. 20A and a zoom-in is shown in FIG. 20B. A rectangular area of size 9×9 pixels is marked over nuclei on the spectral data. The rectangles on cancer and normal nuclei are respectively represented in green and red color. Average transmission spectrums are obtained from these marked rectangles, as each pixel contains spectral information.

Figure 21A:
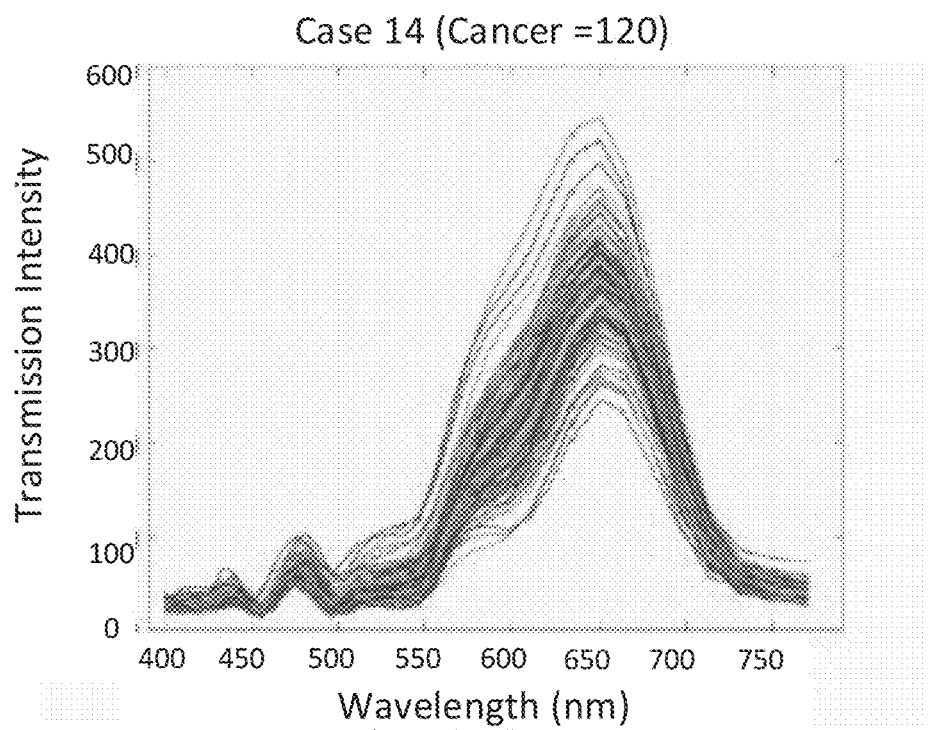
Figure 21B:
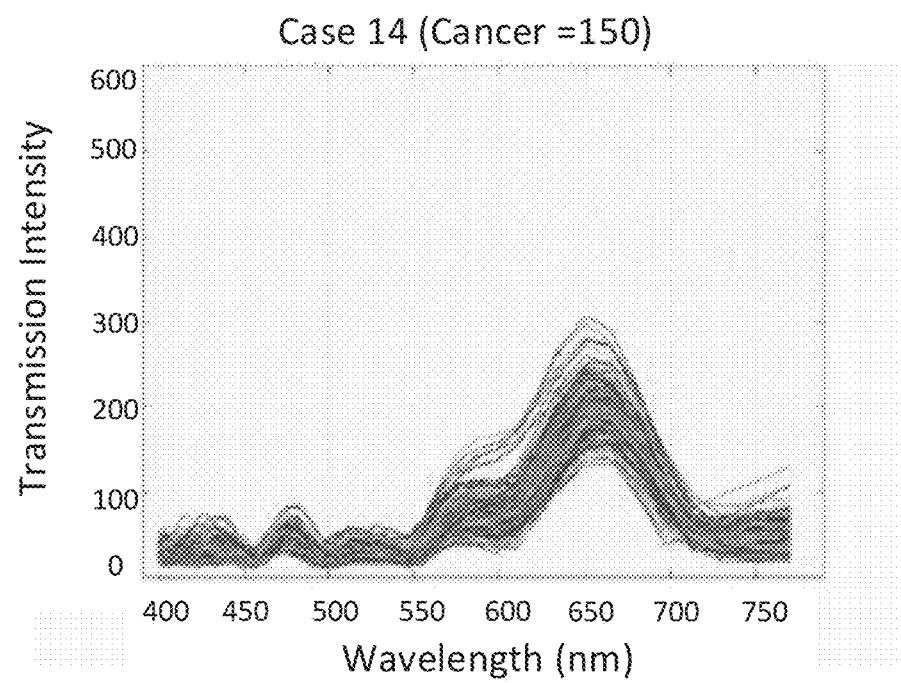
Figure 21C:
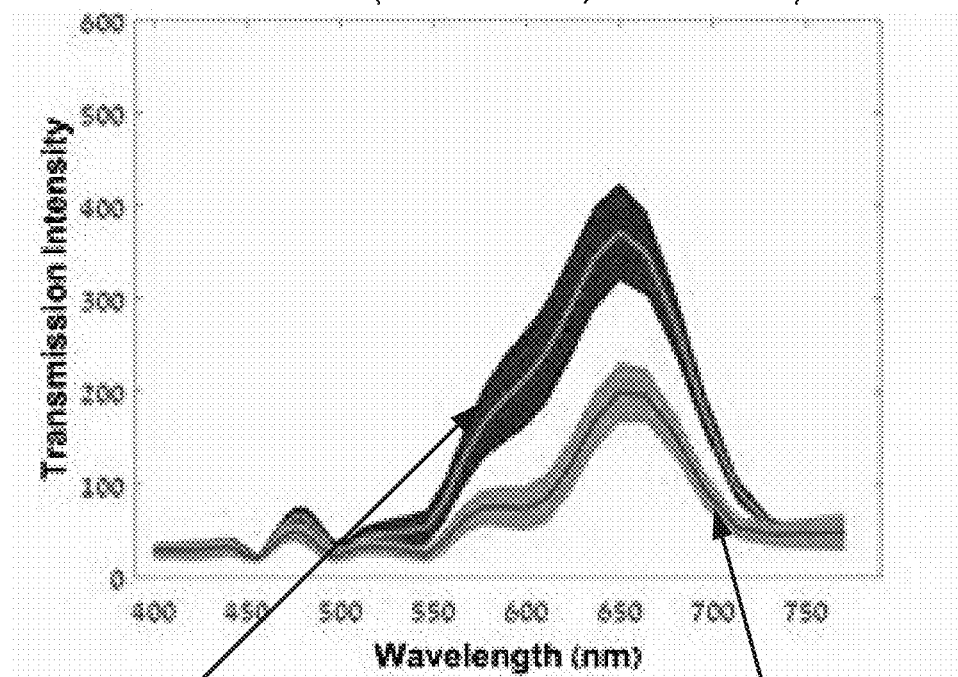
Figure 21D:
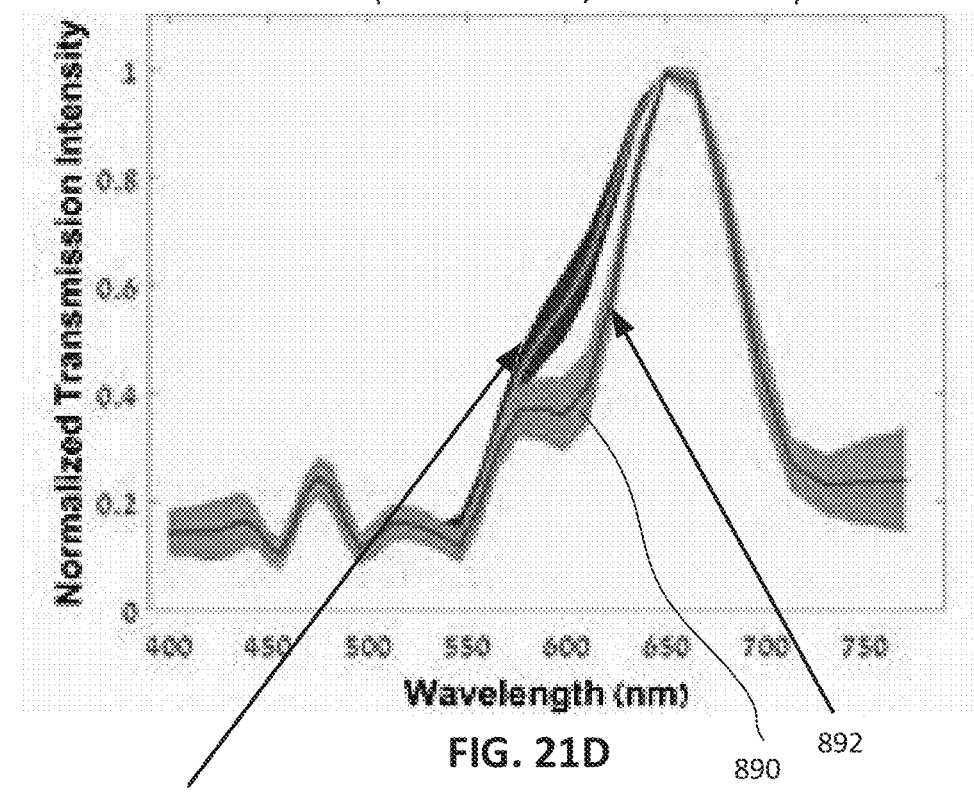

Experimental results for Case 14 are shown in FIGS. 21A, 21B, 21C and 21D. FIG. 21A shows each transmission spectrum retrieved from averaging over 9×9 pixels at each cancer nucleus. FIG. 21B similarly shows each transmission spectrum retrieved after averaging over each normal nucleus with same number of pixels. FIG. 21C shows mean transmission spectrum 891 for cancer (green) obtained from 120 nuclei and a mean transmission spectrum 892 for normal (red) obtained from 150 nuclei. The standard deviation is denoted by shaded region over each mean spectrum. FIG. 21D shows difference in the spectral profile (normalized spectra) for cancer (green) and normal (red).

Clear differences are observed between the transmission spectra of normal and cancer nuclei in the range of 400 nm to 800 nm. Measurement of higher intensity in cancer spectra with a broad spectral profile provided another distinguishable feature. The characteristic absorbance peak of the haematoxylin at 600 nm may indicate the presence of it within the nucleus. It also points toward the physiological transformation that may have occurred in normal cell which becomes cancer, as absorption of haematoxylin increases. A shoulder 890 that appears in the spectrum of normal and is not well defined in the spectra of cancer nuclei originate due to hematoxylin absorption within the nucleus region of each cell. All spectra were marked based on information provided by the pathologist on the stained tissue.

Example 4

FIG. 22A shows a section of tissue singly stained with hematoxylin dye, and marked for normal and cancer nuclei. FIG. 22B shows a subsequent section of tissue singly stained with eosin dye, and similarly marked for normal and cancer nuclei. Example absorption spectra of the normal and cancer nuclei stained with a specific dye is shown in FIGS. 12A, 12B and 12C. Eosin spectra were found not to be much different in normal and cancer tissues, whereas the absorption of hematoxylin showed significant differences between normal and cancer nuclei. Hematoxylin was found to be absorbed significantly more per pixel in the nuclei of normal cells with respect to that of cancer cells. Moreover, when normalizing the spectra so that the spectral features could be emphasized, the most significant difference in the absorption spectrum was found to occur due to an absorption peak at the spectral range of 550-650 nm. This is the characteristic absorption peak of hematoxylin at 600 nm.

Example 5

FIGS. 23A-23J show mean transmission spectrum and difference in the spectral profile for cancer and normal cells for nine different cases. Variability which arises due to biological diversity or other factors within the same case and among different cases was observed, but major differences in the spectra of normal and cancer cells are still well observed and forms the basis for high-efficiency classification. Consistency between the mean spectra for normal and cancer existed in every case.

Example 6

FIG. 24 shows an example scatter plot using a ratio of MSE values for intensity and a ratio of MSE values for shape along the x and y axis respectively as calculated in Equation 5. A total of 414 nuclei are plotted in the scatter plot. If the spectrum of a tested nucleus is more similar to that of a normal cell, then the numerator for both parameters should be rather small, and the denominator should be larger, which means that for a normal cell, both $I_1$ and $I_2$ values should be smaller than 1 (Region I). In contrast, both parameters should be larger than 1 if it is a cancer cell (Region II). The points that correspond to cancer cells are shown in green and the points that correspond to normal cells are shown in red. Almost all normal nuclei in this study were found to be in region marked I where both values are smaller than 1, and almost all cancer cells are in region II where both values are larger than 1.

The classification gave specificity of 95%, sensitivity of more than 90%, and an F-score of 0.96. The nuclei are segmented based on their intensity (calculated as the integrated transmission spectrum at every pixel) before collecting the spectrum and verified manually for achieving accurate statistical analysis. The results indicate on high accuracy even when it is based only on the spectral information without taking into account the nuclei shape, size and other morphological parameters.

Example 7

Average total absorption of the cancer and normal nuclei was determined by calculating a sum of the absorption at every pixel of the nuclei, $A=\Sigma A_i$. The sum was then divided by an average value calculated for normal cells, $A_N=\Sigma A_i/\Sigma A_{N,i}$.

The calculation was performed on 2300 cells. A typical area for cancer cells in the study was found to be 4.3 times that of normal nucleus. The absorbance ratio (Cancer to Normal) was found to be 1.5/2.5. Multiplication with the area of nucleus 4.3 may provide an estimation to the amount of chromatin in cancer nucleus which is 2.56 more than in normal nuclei.

Example 8

Table 1 shows a confusion matrix for all cases based on classification scheme. Percentage of misclassification when normal appears to be cancer or vice-versa is also provided for each case. The results indicates on accuracy of more than 90% even when only the spectral information is taken into account. It demonstrates the quality of the spectral information for cancer detection.

TABLE 1

| A confusion matrix for average of 8 cases based on classification scheme | | | |
|---|---|---|---|
| | | Classification | |
| | True Status | % Normal Cells | % Cancer Cells |
| Average of 8 Cases | Normal | 97.0 | 3.79 |
| | Cancer | 8.22 | 97.03 |

Example 9

FIG. 25 shows examples of spectral unmixing. Row 910 shows example images from case 12. Row 920 shows example images from Case 14. It can be seen that the hematoxylin channel (Ch) attained higher values inside most nuclei, while the eosin channel exhibited the opposite behavior, but in a much less pronounced manner.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of analyzing a spectral image of a sample having cells stained by a stain, the method comprising:
identifying in the spectral image a plurality of nuclei, and extracting, for each nucleus, a spectrum characterizing an optical transmission and absorbance of the nucleus within a wavelength range corresponding to the stain, thereby providing a plurality of spectra, one spectrum for each nucleus of at least a portion of the nuclei;
calculating mean square error relative to a reference spectrum and/or vectorial properties of the spectra in each dimension of a multi-dimensional vector representing the spectra in a multi-dimensional space;
comparing shapes of the spectra thereamongst based on said mean square error and/or said vectorial properties;
identifying each nucleus of the portion of the nuclei, as belonging to one of at least a first population of nuclei and a second population of nuclei based on the comparing; and
marking the nucleus according to the identification.

2. The method of claim 1, comprising identifying each nucleus of the portion of the nuclei, as belonging to one of the first population, the second population and a third population of nuclei, wherein the third population is a set of multiple types of nuclei.

3. The method of claim 1, wherein the first population is cancerous cells and the second population is normal cells.

4. The method of claim 1, further comprising calculating a ratio between mean square error relative to a first reference spectrum and mean square error relative to a second reference spectrum, wherein the comparison is based on the ratio.

5. The method of claim 1,
wherein a parameter associated with spectral intensity is the vectorial properties of the spectra in each dimension of the multi-dimensional space.

6. The method of claim 1, comprising estimating the level of chromatin in cells belonging to each population.

7. A method for protein expression profiling, the method comprising:
labeling a plurality of proteins in a sample having cells stained by a stain;
imaging the sample in accordance with the method of claim 1;
constructing a spectral image based on the imaging;
identifying cancer cells and healthy cells in the spectral image;
detecting intensity of protein expression in the cancer cells and in the healthy cells based on spectral data from the spectral image; and
generating an output pertaining to said detection.

8. The method of claim 7, comprising labeling two proteins with a same label and distinguishing between the expression of the two proteins based on a spatial location of the expression in the cells.

9. The method of claim 4, wherein each mean square error is calculated using non-normalized quantities.

10. The method of claim 9, wherein each mean square error is calculated also using normalized quantities.

* * * * *